United States Patent
Winchell et al.

(10) Patent No.: US 6,264,966 B1
(45) Date of Patent: Jul. 24, 2001

(54) COMPOUNDS WITH CHELATION AFFINITY AND SELECTIVITY FOR FIRST TRANSITION ELEMENTS AND THEIR USE IN COSMETICS AND PERSONAL CARE PRODUCTS, INHIBITION OF METALLOENZYMES, AND INHIBITION OF REPERFUSION INJURY

(75) Inventors: Harry S. Winchell, Lafayette, CA (US); Joseph Y. Klein, Haifa (IL); Elliot D. Simhon, Haifa (IL); Rosa L. Cyjon, Haifa (IL); Ofer Klein, Haifa (IL); Haim Zaklad, Haifa (IL)

(73) Assignee: Concat, Ltd., Concord, CA (US)

( * ) Notice: Subject to any disclaimer, the term of this patent is extended or adjusted under 35 U.S.C. 154(b) by 0 days.

(21) Appl. No.: 09/510,134

(22) Filed: Feb. 22, 2000

(51) Int. Cl.⁷ .............................. A61K 6/00; A61K 7/00; A61K 7/16; A61K 31/675; A61K 31/33
(52) U.S. Cl. ..................... 424/401; 424/49; 424/94.2; 514/79; 514/183; 514/836; 514/900; 514/902
(58) Field of Search ........................... 514/79, 183, 836, 514/900, 902; 424/401, 94.2

(56) References Cited

U.S. PATENT DOCUMENTS

| | | |
|---|---|---|
| 5,236,695 | 8/1993 | Winchell et al. . |
| 5,380,515 | 1/1995 | Winchell et al. . |
| 5,409,689 | 4/1995 | Winchell et al. . |
| 5,874,573 | 2/1999 | Winchell et al. . |

*Primary Examiner*—Frederick Krass
*Assistant Examiner*—Donna Jagoe
(74) *Attorney, Agent, or Firm*—Townsend and Townsend and Crew LLP

(57) ABSTRACT

This invention involves the use of a class of compounds with chelation affinity and selectivity for first transition series elements. Application or administration of the free or conjugated compound, or physiological salts of the free or conjugated compound, results in decrease of the bioavailability and/or chemical action of first transition series elements. These characteristics make such compounds useful in cosmetics and personal care products to decrease odor arising from microbial growth on body surfaces and in body cavities, decrease microbial growth on teeth, plaque, and gums that cause tooth decay and gum disease, inhibition of oxidative damage to the skin, inhibition of enzymatic action of metalloenzymes dependent on first transition series elements, and inhibition of reperfusion injury.

12 Claims, No Drawings

COMPOUNDS WITH CHELATION AFFINITY AND SELECTIVITY FOR FIRST TRANSITION ELEMENTS AND THEIR USE IN COSMETICS AND PERSONAL CARE PRODUCTS, INHIBITION OF METALLOENZYMES, AND INHIBITION OF REPERFUSION INJURY

BACKGROUND AND SUMMARY OF THE INVENTION

All literature and patent citations appearing in this specification are hereby incorporated herein by reference.

First transition series elements are essential to the replication and growth of all cells and viruses. They are essential co-enzymes required in a variety of metabolic processes. Iron and copper can catalyze free radical formation leading to oxidative damage to tissues. Consequently, alterations of the bioavailability and function of first transition series elements can affect cell systems, metabolic processes, and complex phenomena that are affected by such processes.

It is generally appreciated that most body odors arise from chemical byproducts of microbial growth. Thus, antimicrobial agents such as triclosan are commonly added to personal care products and cosmetics to inhibit development of body odors (such as underarm odor) through inhibition of microbial growth. See, *Antiperspirants and Deodorants*, 2d Ed., K. Laden, Ed., 1999, Marcel Dekker, Inc., New York, N.Y.

It is also generally appreciated that tooth decay, gingival inflammation and periodontal disease are initiated by microbial growth on surfaces in the oral cavity. Thus, antimicrobial agents such as triclosan have been incorporated into toothpastes to inhibit such processes. See, *Oral Hygiene Products and Practice*, 1988 Morton Prader, Ed., Marcel Dekker, Inc., New York, N.Y.

It is also generally appreciated that skin aging is, in part, a consequence of cumulative oxidative damage to the skin, particularly related to free radical generation consequent to exposure to solar ultraviolet radiation. In part, such free radical generation occurs through iron-catalyzed Fenton reactions. Thus, personal care/cosmetics preparations have been formulated containing reducing agents such as vitamin E and C to scavenge free radicals and other oxidizing species and it has been proposed that iron chelators be added to sunscreens to inhibit free radical generation. See, *Sunscreens Development Evaluation and Regulatory Aspects*, 1997, N. J. Lowe, N. A. Shaath, M. A. Pothak, Eds., Marcel Dekker, Inc., New York, N.Y.

It is also generally appreciated that first transition series elements act as coenzymes in a variety of enzymatic systems (metalloenzymes). Interference with access to the metal site by agents that chelate, or combine with, the metal at open coordination sites results in inhibition of the enzymatic activity of such enzymes. See, *Inhibition of Matrix Metalloproteinases Therapeutic Applications*, 1999 R. A. Greenwald, S. Zucker, L. M. Golub, Eds., New York Academy of Sciences ANYAA9878 1-761.

It is also generally appreciated that complex tissue processes may be affected by one or more processes in which first transition series elements play a role. For example, reperfusion injury may be related to hydroxyl free radicals arising from iron-catalyzed Fenton reactions (see, "Prevention of Hydroxyl Radical Formation: A Critical Concept for Improving Cardioplegia. Protective Effects of Deferoxamine," P. Menasche, et al., *Circulation*, 1987, vol. 76 (Suppl. V), 180–185) and local release of matrix metalloproteinase enzymes (see, "Inhibition of Matrix Metalloproteinase-2 (MMP-2) Released During Reperfusion Following Ischemia Reduces Myocardial Stunning Injury," G. Sawicki, et al., *Can J. Cardiol.* Vol. 15, Suppl. D, 1999).

Published international patent application WO 97/01360 ("Compounds With Chelation Affinity and Selectivity For First Transition Series Elements, and Their Use in Medical Therapy and Diagnosis," applicant: CONCAT, LTD., publication date Jan. 16, 1997, application number: PCT/US96/10785) discloses compositions and methods relating to a family of chelating agents having high affinity and specificity for first transition series elements. claims include their use in inhibiting bacterial and fungal growth on a surface, including body surfaces, treating conditions dependent on bioavailability of first transition series elements in a patient, and treating conditions that are mediated by free radical or oxidation related tissue destruction.

The present specification demonstrates that the family of chelating agents disclosed in WO 97/01360 are capable of being used in cosmetics and personal care products to inhibit odor development (such as for example underarm odor), to inhibit replication of microorganisms associated with tooth decay and oral disease, and to inhibit oxidation and free radical damage to the skin. This specification also demonstrates that this family of chelating agents is capable of inhibiting enzymatic activity of metalloenzymes containing first transition series elements. Still further, this specification demonstrates that this family of chelating agents inhibits reperfusion injury, possibly as a consequence of their ability to inhibit generation of hydroxyl free radicals and/or inhibition of metalloenzymes such as the matrix metalloproteinases.

This invention resides in the discovery that a class of substituted polyaza compounds showing affinity and selectivity for first transition series elements (atomic numbers 21–30), by virtue of their ability to decrease the bioavailability and/or biochemical action of the first transition series elements, are useful in personal care products to decrease odor arising from microbial growth on body surfaces and in body cavities, decrease microbial growth on teeth, plaque, and gums that cause tooth decay and gum disease, inhibit oxidative damage to the skin, inhibit enzymatic action of metalloenzyme dependent on first transition series elements, and inhibit reperfusion injury. These effects are achieved by application or administration of the substituted polyaza compounds as either free ligands or as conjugated compounds, or as physiological salts of the free ligands or conjugated compounds.

DETAILED DESCRIPTION OF THE INVENTION

Abbreviations

Abbreviations are used herein, in conformation with standard chemical practice, as follows: Bz, benzyl; Me, methyl; Et, ethyl Pr, propyl; $^i$Pr, isopropyl; $^i$Bu, isobutyl; Bu, butyl; $^t$Bu, isopropyl; tertiary-butyl; Ts, para-toluenesulfonyl; Tf$^-$, trifluoroacetate; DMSO, dimethylosulfoxide; DMF, dimethylformamide; DEK, diethyl ketone (3-pentanone); MeOH, methanol; LDA, lithium diisopropylamide; THF, tetrahydrofuran; Py, pyridine; Ac, acetyl; Ac$_2$O, acetic anhydride.

Embodiments of the Invention

This invention provides methods useful in personal care products to decrease odor arising from microbial growth on body surfaces and in body cavities, to decrease microbial growth on teeth, plaque and gums that cause tooth decay and gum disease, to inhibit oxidative damage to the skin, to inhibit enzymatic action of metalloenzymes dependent on first transition series elements, and to inhibit reperfusion injury. The in vivo methods involve administering to a patient or host a chelating agent (or ligand) which is capable of complexing first transition series elements as well as elements with chemical characteristics similar to those of first transition series elements. For the diagnostic methods, the chelating agent is administered as a complex of radio-isotopic or paramagnetic cations of first transition series elements (or those with similar properties).

Among the ligands used in the practice of the present invention are those represented by the following Formulas I through IV:

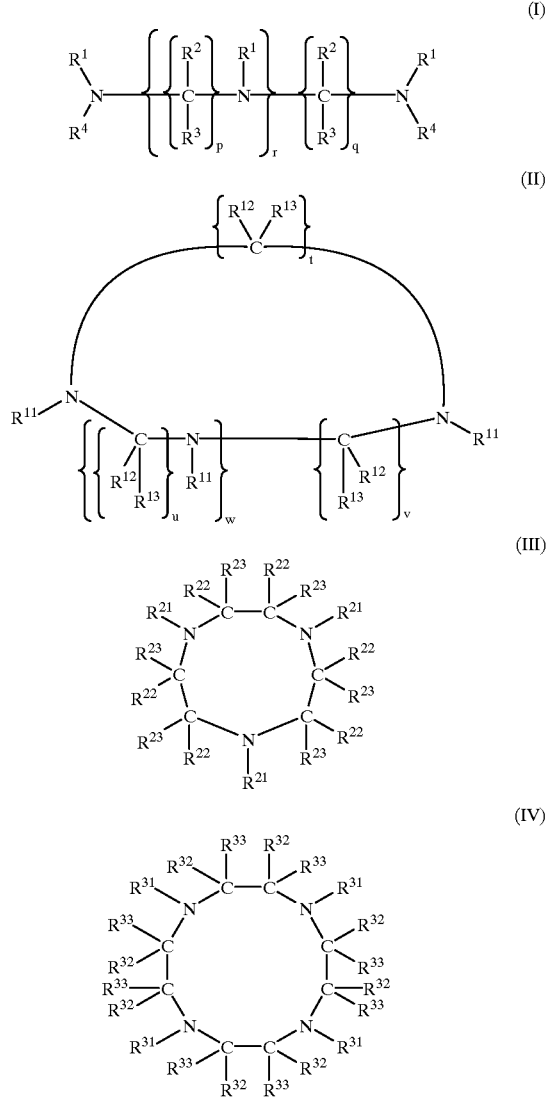

In Formulas I through IV, $R^1$, $R^2$, $R^3$, and $R^4$ may be the same or different on any single molecule, and the same is true for $R^{11}$, $R^{12}$, and $R^{13}$, for $R^{21}$, $R^{22}$, and $R^{23}$, and for $R^{31}$, $R^{32}$, and $R^{33}$. Each of these symbols ($R^1$ through $R^{33}$) represents H, alkyl, alkenyl, aryl, arylalkyl, alkoxy, alkylthio, alkenoxy, alkenylthio, aryloxy, arylthio, alkyl interrupted by one or more oxa (—O—), alkenyl interrupted by one or more oxa (—O—), alkyl interrupted by one or more thia (—S—), alkenyl interrupted by one or more thia (—S—), aryloxyalkyl, alkoxyaryl, aminoalkyl, aminoalkenyl, aminoaryl, aminoarylalkyl, hydroxyalkyl, hydroxyalkenyl, hydroxyaryl, or hydroxyarylalkyl, provided only that these groups that do not interfere with complexation and that they are not combined in a manner that results in a chemically unstable configuration. The alkyl, alkenyl and aryl groups, or portions of groups, in the foregoing list can also be substituted with one or more halogen atoms.

In addition to the radicals and radical subclasses listed above, $R^1$, $R^4$, $R^{11}$, $R^{21}$ and $R^3$ are further defined to include:

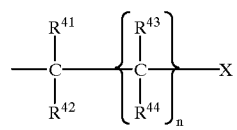

In Formula V, $R^{41}$, $R^{42}$, and $R^{43}$ may be the same or different on any single radical, and are defined as H, alkyl, alkenyl, aryl, arylalkyl, alkoxy, alkylthio, alkenoxy, alkenylthio, aryloxy, arylthio, alkyl interrupted by one or more oxa (—O—), alkenyl interrupted by one or more oxa (—O—), alkyl interrupted by one or more thia (—S—), alkenyl interrupted by one or more thia (—S—), aryloxyalkyl, alkoxyaryl, aminoalkyl, aminoalkenyl, aminoaryl, aminoarylalkyl, hydroxyalkyl, hydroxyalkenyl, hydroxyaryl, or hydroxyarylalkyl, provided only that these groups that do not interfere with complexation and that they are not combined in a manner that results in a chemically unstable configuration. Here again, the alkyl, alkenyl and aryl groups, or portions of groups, in the foregoing list can also be substituted with one or more halogen atoms. $R^{44}$ in Formula V is defined as H, hydroxy, amino, alkyl, alkyl interrupted by oxa (—O—), alkoxy, aryl, aryloxyalkyl, alkoxyaryl, or any of these groups in which the alkyl and aryl portions are substituted with one or more halogen atoms. Again, the groups are selected such that they do not interfere with complexation and are not combined in a manner that results in a chemically unstable configuration.

The index n is either zero or 1.

The symbol X represents any of the following groups:

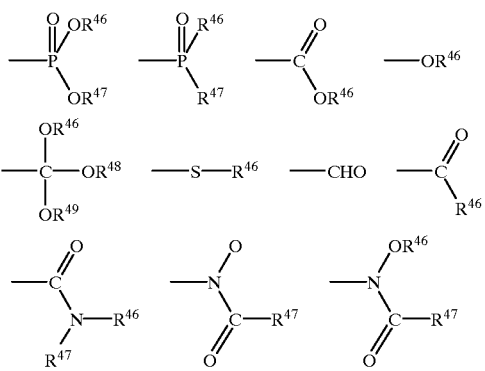

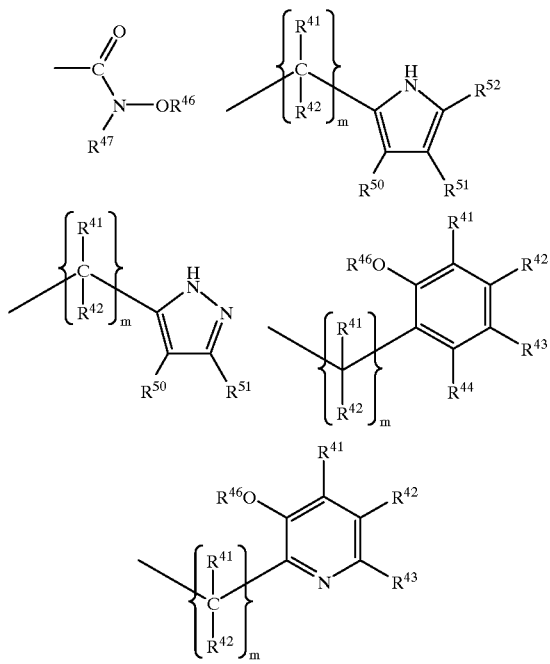

In these formulas, $R^{41}$, $R^{42}$, $R^{43}$, and $R^{44}$ may be the same or different on any single radical, and each has the same definition as that given above for $R^{41}$, $R^{42}$, and $R^{43}$.

$R^{46}$, $R^{47}$, $R^{48}$ and $R^{49}$ may be the same or different on any single radical, and are each defined as H, or alkyl or aryl groups that do not interfere with complexation. $R^{46}$ and $R^{47}$ may further be combined as a single divalent group, thereby forming a ring structure. $R^{48}$ and $R^{49}$ are further defined to include alkoxy, alkyl interrupted by oxa (—O—), aryloxyalkyl, and alkoxyaryl, combine in a manner that results in a chemically stable configuration. All alkyl and aryl groups in this paragraph, including alkyl and aryl portions of groups, are optionally substituted with one or more halogen atoms.

$R^{50}$, $R^{51}$, and $R^{52}$ may be the same or different on any single radical, and are each defined as H, alkyl, alkenyl, aryl, arylalkyl, alkyloxy, alkylthio, alkenyloxy, alkenylthio, aryloxy, arylthio, aminoalkyl, aminoalkenyl, aminoaryl, aminoarylalkyl, hydroxyalkyl, hydroxyalkenyl, hydroxyaryl, or hydroxyarylalkyl.

The index m is an integer which is either 1, 2, or 3.

Returning to Formulas I through IV, further variations within the scope of this invention are as follows:

(1) Internal cyclizations within these formulas at the nitrogen atoms, formed by joining together any two of the $R^1$ and $R^4$ groups in Formula I, any two of the $R^{11}$ groups in Formula II, any two of the $R^{21}$ groups in Formula III, or any two of the $R^{31}$ groups in Formula IV, as a single divalent group bridging the two nitrogen atoms, the single divalent group having the formula $$\left[\begin{array}{c} R^2 \\ | \\ C \\ | \\ R^3 \end{array}\right]_s \quad (VI)$$

in which $R^2$ and $R^3$ are as defined above, and s is at least 2, preferably 2 or 3;

(2) Dimers or other two-molecule combinations of Formulas I through IV (the molecules being the same or different), formed by bridging the molecules together through one or more divalent groups of Formula VI (as defined above) substituted for any one or two of the $R^{11}$ groups in Formula II, any one or two of the $R^{21}$ groups in Formula III, or any one or two of the $R^{31}$ groups in Formula IV;

(3) Internal cyclizations at common carbon atoms within these formulas to form homocyclic rings, by joining one or more of the $R^2$, $R^{12}$, $R^{22}$, or $R^{32}$ groups to one or more of the $R^3$, $R^{13}$, $R^{23}$, or $R^{33}$ groups at the same carbon atom, as a single divalent group of Formula VI (as defined above), and forming one or more such homocyclic rings per structure in this manner; and (4) Internal cyclizations involving two carbon atoms separated by a nitrogen atom within these formulas to form heterocyclic rings, by joining any two adjacent $R^2$ groups in Formula I, any two adjacent $R^{12}$ groups in Formula II, any two adjacent $R^{22}$ groups in Formula III, or any two adjacent $R^{32}$ groups in Formula IV, as a single divalent group of Formula VI (as defined above) and forming one or more such heterocyclic rings per structure in this manner.

In Formula I, the subscripts p and q may be the same or different, and are each either 2 or 3. The subscript r is 0 to 4, inclusive, with the proviso that in the absence of a ring structure r is 1 to 4, inclusive. Preferably, r is 1 or 2.

In Formula II, t, u, and v may be the same or different, and are each either 2 or 3. The value of w is at least 1, more preferably 1 to 4, inclusive, still more preferably 1 to 3, inclusive, and most preferably either 1 or 2.

The terms used in connection with these formulas have the same meaning here as they have in the chemical industry among those skilled in the art. The term "alkyl" thus encompasses both straight-chain and branched-chain groups and includes both linear and cyclic groups. The term "alkenyl" refers to unsaturated groups with one or more double bonds and includes both linear and cyclic groups. The term "aryl" refers to aromatic groups or one or more cycles.

For all such groups, those which are useful in the present invention are those that do not impair or interfere with the formation of the chelate complexes. Within this limitation, however, the groups may vary widely in size and configuration. Preferred alkyl groups are those having 1 to 8 carbon atoms, with 1 to 4 carbon atoms more preferred. Prime examples are methyl, ethyl, isopropyl, n-propyl, and tert-butyl. Preferred aryl groups are phenyl and naphthyl, particularly phenyl. Preferred arylalkyl groups are phenylethyl and benzyl, and of these, benzyl is the most preferred. Preferred cycloalkyl groups are those with 4 to 7 carbon atoms in the cycle, with cycles of 5 or 6 carbon atoms particularly preferred. Preferred halogen atoms are chlorine and fluorine, with fluorine particularly preferred.

One particularly preferred subclass of compounds within Formula I are those in which $R^1$ is alkyl, alkenyl, aryl, arylalkyl, or cycloalkyl, substituted at the β-position with hydroxy. Further preferred are compounds in which one or more, and preferably two or more, of such groups ($R^1$, $R^{11}$, $R^{21}$ and $R^{31}$) on the same formula are substituted at the β-position with hydroxy. Still further preferred are compounds in which the β-hydroxy substituted groups are further substituted at the β-position with at least one hydroxymethyl, alkoxymethyl, alkenoxymethyl, aryloxymethyl, or combinations thereof, all of which may also be further substituted with halogen. Included among these are compounds of Formula III in which one or more of the $R^{21}$ groups are substituted at the β-position with hydroxy and also with hydroxymethyl, alkoxymethyl, alkenoxymethyl, or aryloxymethyl, all of which may also be further substituted with halogen, and the $R^{22}$ and $R^{23}$ groups are all hydrogen atoms.

Certain specific groups for $R^1$, $R^{11}$, $R^{21}$, and $R^{31}$ are particularly preferred. These are 2-hydroxy(2,2-diisopropoxymethyl)ethyl and (3-hydroxy-6,6,7,7-tetramethyl-1,5-dioxacyclohept-3-yl)methyl.

Where indicated, physiologically or pharmacologically compatible salts of the ligands, or complexes thereof, which have an excess of acidic groups are formed by neutralizing the acidic moieties of the ligand with physiologically or pharmacologically compatible cations from corresponding inorganic and organic bases and amino acids. Examples are alkali and alkaline earth metal cations, notably sodium. Further examples are primary, secondary and tertiary amines, notably, ethanolamine, diethanolamine, morpholine, glucamine, N,N-dimethylglucamine, and N-methylglucamine (commonly referred to as "meglumine"). Examples of amino acid cations are lysines, arginines and ornithines.

Similarly, physiologically and pharmacologically compatible salts of those ligands which have an excess of basic groups are formed by neutralizing the basic moieties of the ligand with physiologically or pharmacologically compatible anions from corresponding inorganic and organic acids. Examples are halide anions, notably chloride. Further examples are sulfates, bicarbonate, acetate, pyruvate and other inorganic and organic acids.

Pharmaceutical compositions comprising the chelates described herein are prepared and administered according to standard techniques. The pharmaceutical compositions can be administered parenterally, i.e., intraarticularly, intravenously, subcutaneously, or intramuscularly. Suitable formulations for use in the present invention are found in *Remington's Pharmaceutical Sciences*, Mack Publishing Company, Philadelphia, Pa., 17th ed. (1985).

The chelate compositions can be administered intravenously. Thus, this invention provides compositions for intravenous administration which comprise a solution of the chelate suspended in an acceptable carrier, preferably an aqueous carrier. A variety of aqueous carriers may be used, e.g., water, buffered water, 0.9% isotonic saline, and the like. These compositions may be sterilized by conventional, well known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, calcium chloride, sorbitan monolaurate, triethanolamine oleate, etc.

The concentration of chelates, in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For diagnosis, the amount of chelates in administered complexes will depend upon the particular metal cation being used and the judgement of the clinician. For use in magnetic resonance imaging the dose typically is between 0.05 to 0.5 millimoles/kg body weight.

In general, any conventional method for visualizing diagnostic imaging can be used, depending upon the label used. Usually gamma and positron emitting radioisotopes are used for imaging in nuclear medicine and paramagnetic metal cations are used in magnetic resonance imaging.

The methods of the present invention may be practiced in a variety of hosts. Preferred hosts include mammalian species, such as humans, non-human primates, dogs, cats, cattle, horses, sheep, and the like.

The foregoing description and the following examples are offered primarily for illustration and not as limitations. It will be readily apparent to those of ordinary skill in the art that the operating conditions, materials, procedural steps and other parameters of the compositions and methods described herein may be further modified or substituted in various ways without departing from the spirit and scope of the invention.

EXAMPLES

Example 1

This example illustrates the synthesis of chelators (ligands) which are useful in the present invention. Section 1.1 illustrates the synthesis of polyaza bases. Section 1.2 illustrates the synthesis of alkylating groups. Section 1.3 illustrates the preparation of chelating agents from alkylation of polyaza bases.

In all examples reactions were carried out in common solvents, compounds were purified by routine methodology and identity was established by proton NMR. In some cases identity was further verified by elemental analysis, mass spectroscopy, C-13 or P-31 NMR, or by synthesis of the identical compound by an independent alternate synthesis route.

1.1 SYNTHESIS OF POLYAZA BASES

Ethylene diamine (1.1.0), diethylene triamine (1.1.1), triethylenetetramine (1.1.2), 1,4,7-triazacyclononane (1.1.3), 1,4,7,10-tetraazacyclododecane (1.1.4), 1,4,8,11-tetraazacyclotetradecane (1.1.5) & 1,5,9,13-tetraazacyclohexadecane (1.1.6) and the corresponding hydrohalide salts were either obtained from commercial sources or were synthesized employing established methods and were used directly in the syntheses of chelators (ligands) described in section 1.3. Additional polyaza bases were synthesized as described herein.

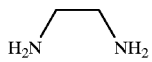

1.1.0

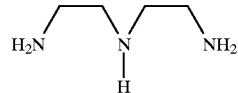

1.1.1

-continued

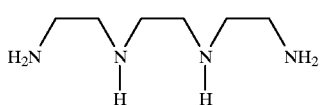
1.1.2

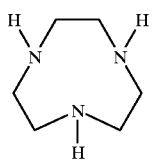
1.1.3

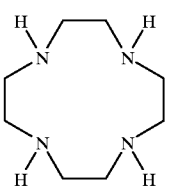
1.1.4

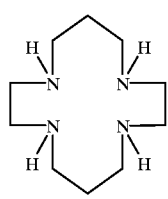
1.1.5

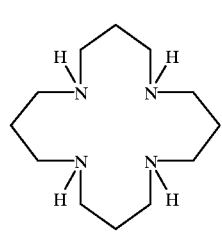
1.1.6

1.1.7 2,6-Diethyl-1,4,7-triazacyclononane trihydrobromide 2-(p-toluenesulfonylamino)-1-(p-toluenesulfonyloxy)butane (1.1.8) and ammonium hydroxide were reacted to form 2-(p-toluenesulfonamino)-1-aminobutane (1.1.9). This was reacted with 2-(p-toluenesulfonylamino)-1-(p-toluenesulfonyloxy)butane (1.1.8) and potassium carbonate. The 3,7 bis(p-toluenesulfonylamino)-5-azanonane (1.1.10) product was purified by chromatography and reacted with p-toluenesulfonyl chloride to obtain the corresponding tri-p-toluenesulfonyl compound 3,7 bis(p-toluenesulfonylamino)-5-(p-toluenesulfonyl-5-azanonane (1.1.11). This was purified by chromatography and reacted with 2.2 equivalents of sodium amide in DMF and then with 1,2-di(p-toluenesulfonyloxy)ethane (1.1.1 2). The 2,6-diethyl-1,4,7-tris(p-toluenesulfonyl) triazacyclononane (1.1.13) that was obtained following purification was heated in a solution of HBr in acetic acid to remove the p-toluenesulfonyl groups and form the titled compound (1.1.7)

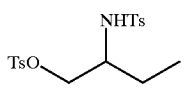
1.1.8

-continued

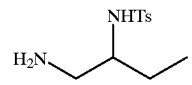
1.1.9

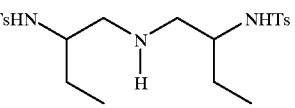
1.1.10

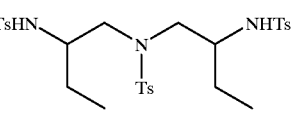
1.1.11

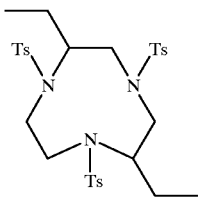
1.1.12

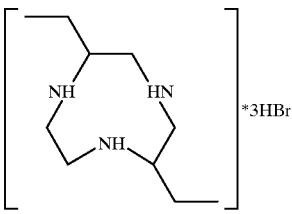
1.1.13

1.1.17

1.1.14 1,4,7-Triazabicyclo[7.4.0$^{8,13}$]tridecane trihydrobromide 1,2-trans-bis(p-toluenesulfonylamino)cyclohexane (1.1.15) was treated with NaH in DMSO. 1-(p-toluenesulfonylamino)-2-(p-toluenesulfonyl) ethane (1.1.16) was added to obtain 1-(p-toluenesulfonylamino)-2-[N-p-toluenesulfonyl-N-(2-p-toluenesulfonylaminoethyl)]aminocyclohexane (1.1.17). This was separated and reacted with NaH and 1,2-di(p-toluenesulfonyloxy)ethane (1.1.12) was added. The 2,3-butano-N,N'N"-tris(p-toluenesulfonyl)-1,4,7-triazacyclononane (1.1.18) obtained was purified by chromatography. The p-toluenesulfonyl groups were removed by reaction in HBr/Acetic acid and the 2,3-butano-1,4,7-triazacyclononane trihydrobromide (1.1.14) product precipitated from solution as the hydrobromide salt.

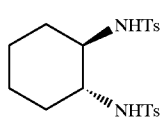
1.1.15

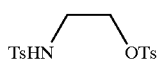
1.1.16

1.1.17
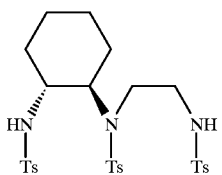

1.1.18
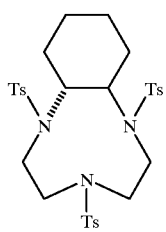

1.1.14
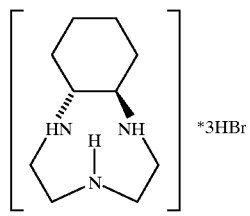

1.1.19 1,3-Bis (1,4,7-triazacyclononane) propane N,N'-bis(p-toluenesulfonyl)-1,4,7-triazacyclononane (1.1.20) was prepared by reacting (1.1.3) with two equivalents of p-toluenesulfonyl chloride. Two equivalents of N,N'-bis(p-toluenesulfonyl)-1,4,7-triazacyclononane (1.1.20) hydrobromide were reacted with one equivalent of 1,3-diiodopropane in acetonitrile with excess potassium carbonate. 1,3-Bis[N,N'-bis(p-toluenesulfonyl)-1,4,7-triazacyclononane propane (1.1.21) was isolated and purified by chromatography. The p-toluenesulfonyl groups were removed using sulfuric acid and HBr to yield the title compound (1.1.19).

1.1.20
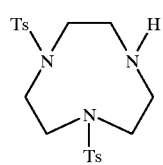

1.1.21
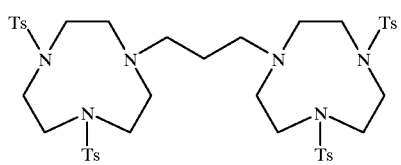

1.1.19
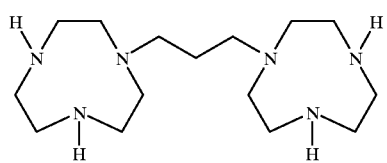

1.1.22 1,4,7,10-Tetraazabicyclo[5.5.2]tetradecane 1,4,7,10-tetraazadodecane (1.1.4) trihydrobromide in acetonitrile with potassium carbonate was reacted with glyoxal to form 1,4,7,10-tetraazatetracyclo-[5,5,2,0$^{4,13}$,0$^{10,14}$] tetradecane (1.1.23). Following separation the pure product was obtained by low pressure distillation. This was dissolved in acetonitrile and benzylbromide was added to form 1,7-dibenzylonium-1,4,7,10-tetraazatetracyclo[5,5,2,0$^{4,13}$,0$^{10,14}$] tetradecane (1.1.24). Following recrystallization from ethanol this was reacted with sodium borohydride. HCl was added, followed by water and NaOH, and the product extracted with chloroform. Following evaporation of solvent the solids were dissolved in methanol and HBr was added to obtain 1,7-dibenzyl-1,4,7,10-tetraazabicyclo [5.5.2] tetradecane (1.1.25) as the hydrobromide salt. This was dissolved in water and reduced using H$_2$ and a Pd-C catalyst to remove the benzyl groups. Purification of the title compound was by crystallization of the hydrobromide salt. The base form was obtained by low pressure distillation following addition of base.

1.1.23
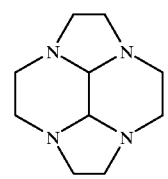

1.1.24
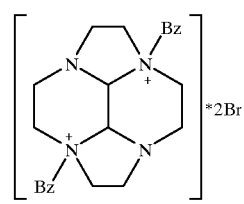

1.1.25
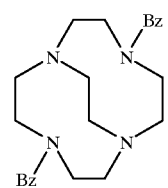

1.1.22
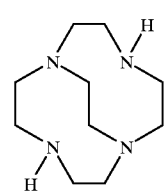

1.1.26 1,4,7,10,13-Pentaazabicyclo [8.5.2] heptadecane.

To 1,8-bis(p-toluenesulfonyloxy)-3,6-bis(p-toluenesulfonyl)-3,6-diazaoctane(1.1.27) was added 1,4,7-triazacyclononane(1.1.3) in acetonitrile with potassium bicarbonate to obtain 4,7-bis (p-toluenesulfonyl)-1,4,7,10,13-pentaazabicyclo [8.5.2] (1.1.28) heptadecane. The title compound was purified and the p-toluenesulfonyl groups were removed by treatment in sulfuric acid. Purification was done by low pressure distillation.

1.1.27
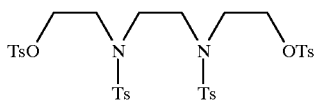

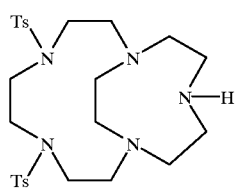

1.1.28

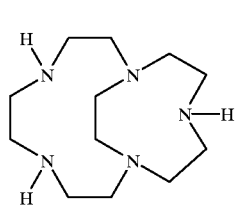

1.1.26

1.1.29 1,2-Bis(1,4,7-triazabicyclononane-1-yl) ethane.

A mixture of N,N'-bis(p-toluenesulfonyl)-1,4,7-triazabicyclonone hydrobromide (1.1.13.33), ethylene glycol di-p-toluenesulfonyl or dibromoethane and excess of potassium carbonate in acetonitrile was refluxed overnight. The reaction mixture was added to water and extracted with methylene chloride. The tetratosylated product (1.1.30) was purified by chromatography. It was suspended in 70% $H_2SO_4$ and heated at 150° C. for 15 hrs. The reactions cooled to room temperature and then 62% HBr solution was added. The white precipitate was collected and washed with ethanol. It was redissolved in water and filtered from tars. The water was made basic and the title compound (1.1.29) was extracted with chloroform.

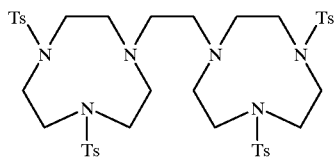

1.1.30

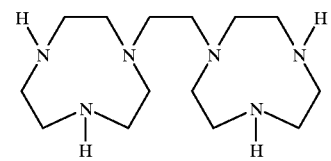

1.1.29

1.2 SYNTHESIS OF ALKYLATING GROUPS FOR ALKYLATION OF POLYAZA BASES TO FORM CHELATORS DESCRIBED IN EXAMPLE 1.3.

1.2.1 Preparation of Glycidyl Ethers

Glycidyl tosylate (R, S or d,l) (1.2.1.0) was reacted in the appropriate alcohol solvent employing catalytic amounts of conc. $H_2SO_4$ or equivalent amounts of tetrafluoroboranetherate. The 1-alkyloxy-2-hydroxy-3-p-toluenesulfonyloxypropane (1.2.1.1) product was reacted in ether with BuLi to yield the title epoxide. The following compounds were prepared in this manner.

1.2.1.0 Glycidyl tosylate (R,S or d,l; commercially available).

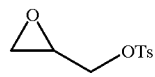

1.2.1.0

1.2.1.1 1-Alkyloxy-2-hydroxy-3-p-toluenesulfonyloxypropane.

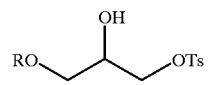

1.2.1.1

1.2.1.2 d,l-Glycidyl-isopropyl ether (commercially available).

1.2.1.2

1.2.1.3 (2R) Glycidyl-isopropyl ether.

1.2.1.4 (2S) Glycidyl-isopropyl ether.

1.2.1.5 d,l-Glycidyl-t-butyl ether.

1.2.1.5

1.2.1.6 (2R) Glycidyl-t-butyl ether.

1.2.1.7 d,l-Glycidyl allyl ether.

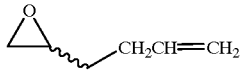

1.2.1.7

1.2.1.8 d,l-Glycidyl phenyl ether

1.2.1.8

1.2.2 Preparation of 2,2-Dialkoxymethylene Oxiranes and Spiro-Oxiranes

3-Chloro-2-chloromethyl-1-propane (1.2.2.0) was reacted with the corresponding sodium alkylate or disodium dialkylate either using the same alcohol or dialcohol as solvent or using an inert solvent. The ether product was purified by distillation or chromatography. Epoxidation was performed using meta-chloroperbenzoic acid in halogenated solvent. The following compounds were prepared in this manner.

1.2.2.0 3-Chloro-2-chloromethyl-1-propane (commercially available).

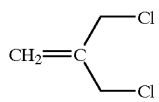

1.2.2.0

1.2.2.1. 2,2-Bis-ethoxymethyl oxirane.

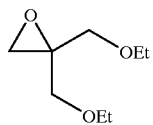

1.2.2.1

1.2.2.2 2,2-Bis-methoxymethyl oxirane.

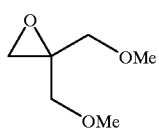

1.2.2.2

1.2.2.3 2,2-Bis-isopropyloxymethyl oxirane.

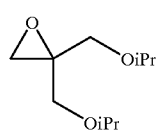

1.2.2.3

1.2.2.4 2,2-Bis-difurfuryloxymethyl oxirane.

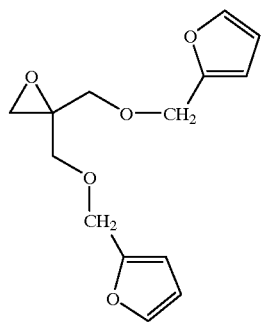

1.2.2.4

1.2.2.5 2,2-Bis(hydroxymethyl) oxirane
From 2-methylidene-1,3-dihydroxypropanediol (commercially available).

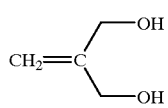

1.2.2.5

1.2.3 Preparation of Oxiranespiro-3-(1,5-Dioxacycloalkanes).
Various dry glycols in DMF were reacted with NaH and 3-chloromethyl-1-propane (1.2.2.0) was added to the resulting reaction mixture. Following completion of the reaction the solvents were removed and the product purified by low pressure distillation. The purified product in dichloroethane was reacted with m-chloroperbenzoic acid to form the corresponding epoxide. Following workup, the epoxide product was purified by distillation. The following compounds were prepared in this manner.

1.2.3.1 Oxiranespiro-3-(1,5-dioxacycloheptane).

(From ethylene glycol)

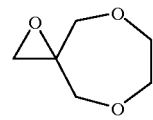

1.2.3.1

1.2.3.2 Oxiranespiro-3-(1,5-dioxa-7,7-dimethylcyclooctane).

(From 2,2-dimethyl propylene glycol)

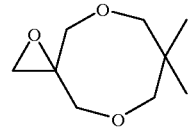

1.2.3.2

1.2.3.3 Oxiranespiro-3-(1,5-dioxa-6-methylcycloheptane).

(From 1,2-dihydroxy propane)

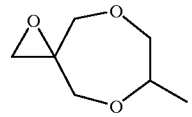

1.2.3.3

1.2.3.4 Oxiranespiro-3-(1,5-dioxa-6,6,7,7-tetramethylcycloheptane).

[From 2,3-dihydroxy-2,3-dimethyl butane (pinacol)].

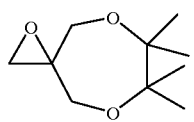

1.2.3.4

1.2.3.5 Oxiranespiro-3-(benzo [b]-1,5-dioxacycloheptane).

(From 1,2-dihydroxybenzene).

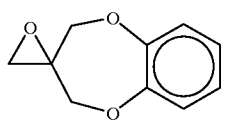

1.2.3.5

1.2.3.6 Oxiranespiro-3-(1,5-dioxacycloctane).

(From 1,3-propanediol)

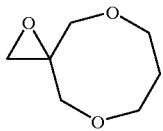

1.2.3.6

1.2.4 Preparation of Miscellaneous Epoxides

1.2.4.1 2,2-dimethyl oxirane.

(From 2-methyl-1-propene and m-chloroperbenzoic acid.

1.2.4.1

1.2.4.2 2-(Isopropyl)-2-[(1-fluoro-1-methyl)ethyl] oxirane.

Reaction between 2,4-dimethyl-3-pentanone (1.2.4.3), trimethylsilyl chloride, and base gave 2,4-dimethyl-3-trimethysilyloxy-2-pentene (1.2.4.4) which was reacted with 1-fluoropyridinium triflate (1.2.4.5) to form 2,4-dimethyl-2-fluoro-3-pentanone (1.2.4.6). This product was reacted with $(CH_3)_3S(O)^+I^-$ to form the title compound (1.2.4.2).

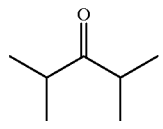

1.2.4.3

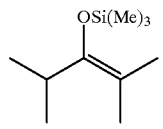

1.2.4.4

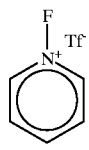

1.2.4.5

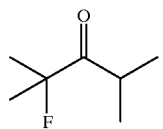

1.2.4.6

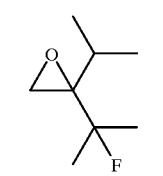

1.2.4.2

1.2.4.7 2,2-Bis-isopropyl oxirane.

(From 2,4-dimethylpentanone using $(CH_3)_3S(O)^+I^-$ as described in 1.2.4.2)

1.2.4.7

1.2.4.8 2-(1-Fluoroethyl)-2-(1-trimethylsilyloxyethyl) oxirane.

The title compound was obtained in several steps. DEK was O-silylated using usual procedure. The resulting product was reacted with 1-fluoropyridinium triflate (1.2.4.5) to yield 2-fluoro-3-pentanone (1.2.4.9). After bromination the 2-bromo-4-fuoro-3-pentanone (1.2.4.10) which was obtained was reacted with liquid ammonia to form 2-fluoro-4-hydroxy-3-pentanone (1.2.4.11). The free hydroxyl group was protected with trimethylsilylchloride to form 2-fluoro-4-trimethylsilyloxo-3-pentanone (1.2.4.12). This product was reacted with trimethylsulfoxonium iodide to form the title compound (1.2.4.8).

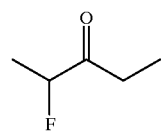

1.2.4.9

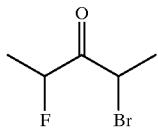

1.2.4.10

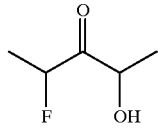

1.2.4.11

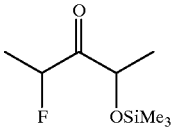

1.2.4.12

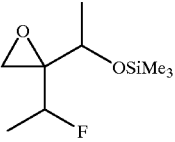

1.2.4.8

1.2.4.13 2-(1-Bromoethyl)-3-methyl oxirane.

Bromination of diethyl ketone with bromine gave 2,4-dibromo-3-pentanone (1.2.4.14). This product was reduced with $BH_3$/THF to form 3-hydroxy-2,4-dibromopentane (1.2.4.15). After treatment with base the title compound (1.2.4.13) was obtained.

1.2.4.14

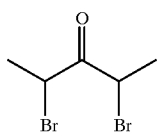

1.2.4.15

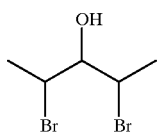

1.2.4.13

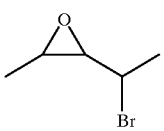

1.2.4.16 2-(1-Fluoroethyl)-3-methyl oxirane.

From reaction between diethylketone and trimethylchlorosilane to form 3-trimethylsilyloxy-2-pentene (1.2.4.17). This product was reacted with 1-fluoropyridinium triflate (1.2.4.5) to obtain 2-fluoro-3-pentanone (1.2.4.9). After bromination with pyridinium bromide followed by reduction using diborane 2-fluoro-4-bromopentane-3-ol (1.2.4.18) was obtained. Reaction of this product with sodium methylate yielded the title compound (1.2.4.16). This compound was made also by reacting 2-(1-bromoethyl)-3-methyl oxirane (1.2.4.13) with HF/Py (70%) followed by treatment of the resulting 2-bromo-4-fluoropentan-3-ol (1.2.4.18) with $K_2CO_3$/MeOH.

1.2.4.19 2-(1-Fluoroethyl)-2-(1-methoxyethyl) oxirane.

1.2.4.17

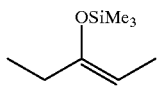

1.2.4.18

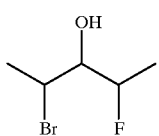

1.2.4.16

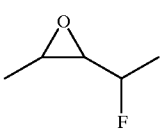

2-(1-Fluoroethyl)-3-methyl oxirane (1.2.4.16) was reacted with methanol/sulfuric acid to obtain 2-fluoro-4-methoxypentane-3-ol (1.2.4.20). This product was reacted with chromic anhydride/pyridine to form 2-fluoro-4-methoxypentane-3-one (1.2.4.21) which was then reacted with sodium hydride and trimethylsulfoxonium iodide to obtain the title compound (1.2.4.19).

1.2.4.20

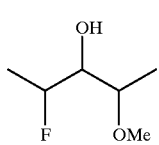

1.2.4.21

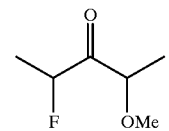

1.2.4.19

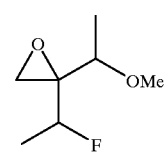

1.2.4.22 2-(1-Methoxyethyl)-3-methyl oxirane.

Reaction of 2-(1-Bromoethyl)-3-methyl oxirane (1.2.4.13) with methanol/sulfuric acid formed 2-bromo-3-hydroxy-4-methoxypentane (1.2.4.23). This product was reacted with potassium carbonate in methanol to obtain the title compound (1.2.4.22).

1.2.4.23

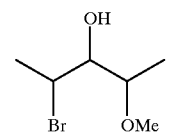

1.2.4.22

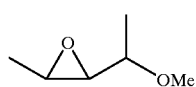

1.2.4.24 2-Ethyl-2-(1-methoxyethyl) oxirane.

Reaction between diethyl ketone and dimethyl hydrazine gave diethyl ketone-N,N-dimethylhydrazone (1.2.4.25). This product was reacted with dimethyl disulfide/LDA to obtain 2-methylthio-3-pentanone-N,N-dimethyl hydrazone (1.2.4.26). This product was reacted with mercuric chloride followed by cupric chloride to obtain 2-methoxy pentane-3-one (1.2.4.27). Reaction of the latter compound with sodium hydride/DMSO/trimethylsulfonium iodide yielded the title compound (1.2.4.24).

1.2.4.25

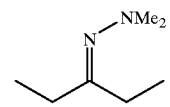

1.2.4.26

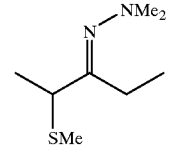

1.2.4.27

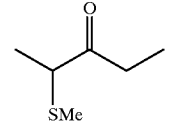

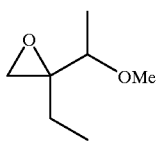

1.2.4.28 2-Ethyl-2-(1-trimethylsilyloxyethyl) oxirane.

From reaction between 2-bromo-3-pentanone (1.2.4.29) and hydrazine obtained 2-hydroxy-3-pentanone (1.2.4.30). This product was reacted with trimethylchlorosilane/ triethylamine to obtain 2-trimethylsilyloxy-3-pentanone (1.2.4.31). This product was reacted with methylenetriphenyl phosphite and butyllithium to obtain 2-ethyl-3-trimethylsilyloxy-1-butene (1.2.4.32). After oxidation with meta-chloroperbenzoic acid in methylene chloride the title compound (1.2.4.28) was obtained.

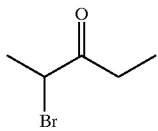

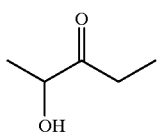

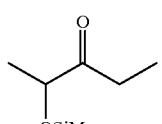

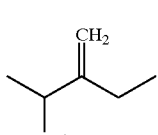

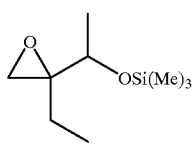

1.2.4.33 2,2-Bis(1-fluoroethyl) oxirane.

From reaction between 2-(1-Bromoethyl)-3-methyl oxirane (1.2.4.13) and HF/pyridine was obtained 2-bromo-4-fluoro-pentane-3-ol (1.2.4.18). This was reacted with potassium carbonate to obtain 2-(1-fluoroethyl)-3-methyl oxirane (1.2.4.16). This was reacted again with HF/pyridine to obtain 2,4-difluoro-pentane-3-ol (1.2.4.34). After oxidation with chromium trioxide obtained 2,4-difluoro-3-pentanone (1.2.4.35). The epoxide title compound was prepared from the ketone as described for 1.2.4.24.

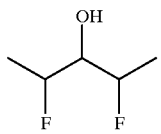

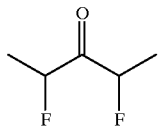

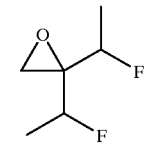

1.2.3.36 2,2-Bis-dichloromethyleneoxirane.
(From direct epoxidation of 3-chloro-2-chloromethyl-1-propene).

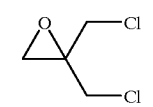

1.2.4.37 2,2-Bis(1-methoxyethyl) oxirane.

3-Pentanone was brominated to get 2,4-dibromo-3-pentanone (1.2.4.11) using conventional methods. The dibromoketone was reduced with $BH_3 \cdot THF$ to the corresponding alcohol (1.2.4.15). This compound was reacted with MeONa in methanol to yield 2-(1-bromoethyl)-3-methyl oxirane (1.2.4.13) which after reaction with MeOH/$H_2SO_4$ gave 2-bromo-3-hydroxy-4-methoxy pentane (1.2.4.38). This intermediate was reacted again with MeONa in methanol and the resulting 2-(1-methoxyethyl)-3-methyl oxirane (1.2.4.22) was reacted again with MeOH/$H_2SO_4$ to yield 2,4-dimethoxy-3-hydroxy pentane (1.2.4.39). After oxidation with $CrO_3$/Py in methylenechloride the resulting ketone was reacted with trimethylsulfoxonium iodide to give the title compound (1.2.4.37).

1.2.6.2 1-Bromo-2-t-butyldimethylsilyloxyethane, $BrCH_2CH_2Si(^tBu)(CH_3)_2$ (From bromoethanol and dimethyl-t-butylsilylchloride)

1.2.6.3 5-(p-Toluenesulfonyloxymethylene)-1-benzyloxy-2-pyrrolidone.

This compound was prepared in several steps. 4-pentenoic acid (1.2.6.4) was reacted with ethylchloroformate in the usual way to obtain the active mixed anhydride. To a solution of the mixed anhydride in chloroform was added triethylamine and O-benzylhydroxylamine hydrochloride to obtain O-benzyl-4-pentenohydroxamic acid (1.2.6.5). The double bond was oxidized using osmium tetroxide/N-methylmorpholine oxide to give the diol (1.2.6.6). The terminal hydroxyl group was then protected with t-butyldimethylsilylchloride in the usual way to yield (1.2.6.7). The secondary hydroxyl group was tosylated using pyridine/p-toluenesulfonyl chloride. Cyclization of (1.2.6.8) to the corresponding pyrrolidone (1.2.6.9) was effected by using sodium carbonate in methanol. The protecting silyl group was removed by treatment with tetraethylammonium fluoride. The title compound (1.2.6.3) was prepared by reacting the latter compound (1.2.6.10) with pyridinelp-toluenesulfonyl chloride in the usual way.

1.2.6.4: CH2=CHCH2CH2COOH 1.2.6.5: CH2=CHCH2CH2CONHOBz 1.2.6.6: HOCH2CH(OH)CH2CH2CH2CONHOBz 1.2.6.7: tBu(Me)2SiO-CH2CH(OH)CH2CH2CH2CONHOBz 1.2.6.8: tBu(Me)2SiO-CH2CH(OTs)CH2CH2CH2CONHOBz 1.2.6.9: iBu(Me)2SiO-[N(OBz)-pyrrolidinone]

1.2.6.10: HOCH2-[N(OBz)-pyrrolidinone]

1.2.6.3: TsOCH2-[N(OBz)-pyrrolidinone]

1.2.6.11 5-Bromo-1-benzyloxy-2-pyrrolidone.

This compound was prepared in several steps. Butyrolactone was reacted with PBr3/Br2 to obtain the dibromobutyrylbromide (1.2.6.12). This compound with O-benzylhydroxylamine yielded the protected dibromohydroxamic acid (1.2.6.13). Cyclization was effected by base to give the cyclic protected hydroxamic acid (1.2.6.11).

1.2.6.12: Br-CH2CH2-CH(Br)-C(O)-Br 1.2.6.13: Br-CH2CH2-CH(Br)-C(O)-NH-OBz 1.2.6.11: [OBz-N-pyrrolidinone with Br at 5-position]

1.2.7 Preparation of N-Alkyl-O-Benzylchloroacetohydroxamic Acids.

This class of compounds was prepared from chloroacetyl chloride and the suitable N-Alkylhydroxylamine followed by O-benzylation with benzyl bromide. In certain instances the O-benzyl alkylhydroxylamine was used as the starting material. O-Methyl chloroacetoxyhydroxamic acid was prepared employing O-methylhydroxylamine as starting material.

1.2.7.1 O-Benzyl-N-Methyl Chloroacetohydroxamic acid, ClCH$_2$CON(Me)(OBz).

1.2.7.2 O-Benzyl-N-isopropyl-Chloroacetohydroxamic acid, ClCH$_2$CON($^i$Pr)(OBz).

1.2.7.3 O-Benzyl-N-tert-butyl-Chloroacetohydroxamic acid, ClCH$_2$CON($^t$Bu)(OBz).

1.2.7.4 O-Benzyl Chloroacetohydroxamic acid, ClCH$_2$CONH(OBz)

1.2.7.5 O-Methyl chloroacetohydroxamic acid, ClCH$_2$CONH(OMe)

1.3 SYNTHESIS OF CHELATORS (LIGANDS)

1.3.1 Synthesis of Polyaza Ligands with Pendant Arms Containing β-Hydroxy Groups and Their Derivatives.

This family of compounds was prepared by reacting polyaza free bases with epoxides or halohydrines in water or alcohol solvents.

1.3.1.1 N,N',N"-Tris(2-hydroxy-3-isopropoxypropyl)-1,4,7-Triazacyclononane.

From 1,4,7-triazacyclononane (1.1.3) and d,l-glycidyl isopropyl ether (1.2.1.2).

1.3.1.1: [1,4,7-triazacyclononane with three iPrOCH$_2$CH(OH)CH$_2$- pendant arms]

1.3.1.2 (R,R,R) N,N',N"-Tris(2-hydroxy-3-isopropoxypropyl)-1,4,7-triazacyclononane.

From 1,4,7-Triazacyclononane (1.1.3) and (2R) glycidyl isopropyl ether (1.2.1.3).

1.3.1.2

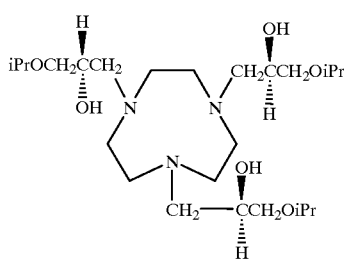

1.3.1.3 (S,S,S) N,N',N"-Tris(2-hydroxy-3-isopropoxypropyl)-1,4,7-triazacyclononane.

From 1,4,7-Triazacyclononane and (2S) glycidyl isopropyl ether (1.2.1.4).

1.3.1.3

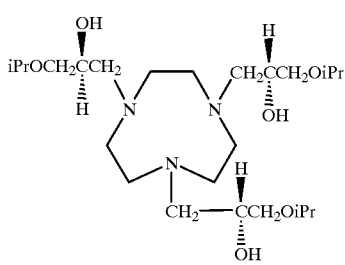

1.3.1.4 N,N',N"-Tris(2-hydroxy-3-t-butoxypropyl)-1,4,7-triazacyclononane.

From 1,4,7-Triazacyclononane (1.13) and (d,l) glycidyl-t-Butyl ether (1.2.1.5).

1.3.1.4

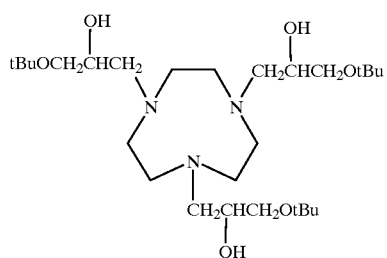

1.3.1.5 (R,R,R) N,N',N"-Tris(2-hydroxy-3-t-butoxypropyl)-1,4,7-triazacyclononane.

From 1,4,7-triazacyclononane (1.1.3) and (R) glycidyl t-Butyl ether (1.2.1.6).

1.3.1.5

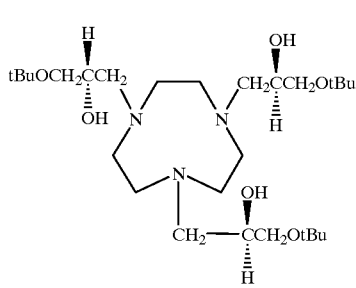

1.3.1.6 N,N',N"-Tris(2-hydroxy-3 methoxypropyl)-1,4,7-triazacyclononane

From 1,4,7-Triazacyclononane (1.1.3) and (d,l) glycidyl methyl ether (commercially available).

1.3.1.6

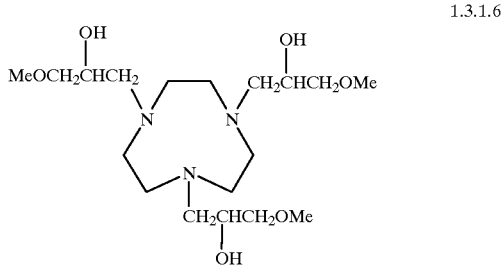

1.3.1.7 N,N',N"-Tris(2,3-dihydroxypropyl)-1,4,7-triazacyclononane.

From 1,4,7-triazacyclononane (1.1.3) and 1-bromo-2,3-dihydroxypropane (commercially available) and excess of potassium carbonate or 1-chloro-2,3-dihydroxypropane (commercially available) and base.

1.3.1.7

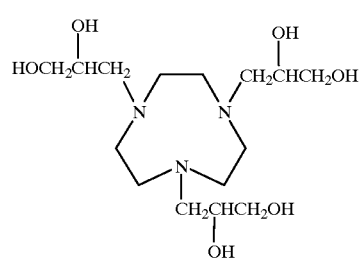

1.3.1.8 N,N',N"-Tris(1-methoxy-2-hydroxy-2-methylpropyl)-1,4,7-triazacyclononane.

From 1,4,7-Triazacyclononane (1.1.3) and (d,l) 3,3-Dimethyl-2-methoxy oxirane (1-methoxy-2-methylpropylene, commercially available).

1.3.1.8

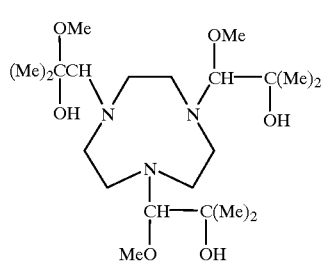

1.3.1.9 N,N',N"-Tris(2-hydroxy-3-allyloxypropyl)-1,4,7-triazacyclononane.

From 1,4,7-Triazacyclononane (1.1.3) and (d,l) glycidyl allyl ether (1.2.1.7).

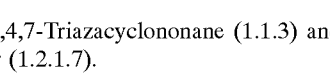

1.3.1.9

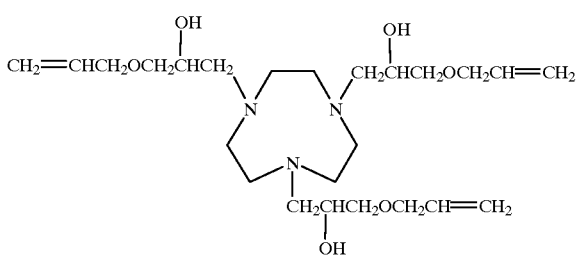

1.3.1.10 N,N',N"-Tris(2-hydroxy-3-phenoxypropyl)-1,4,7-triazacyclononane.

From 1,4,7-Triazacyclononane (1.1.3) and (d,l) glycidyl phenyl ether (1.2.1.8).

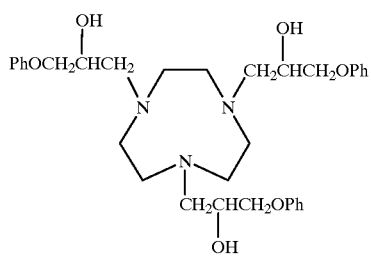

1.3.1.11 N,N',N"-Tris(2-hydroxy-2,2-diethoxymethylene)ethyl-1,4,7-triazacyclononane.

From 1,4,7-triazacyclononane (1.1.3) and 2,2-Bis-ethoxymethyl oxirane(1.2.2.1).

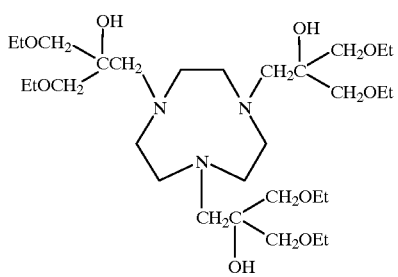

1.3.1.12 N,N',N"-Tris(2-hydroxy-2,2-dimethoxymethyl)ethyl-1,4,7-triazacyclononane.

From 1,4,7-triazacyclononane (1.1.3) and 2,2-Bis-methoxyoxymethyl oxirane (1.2.2.2).

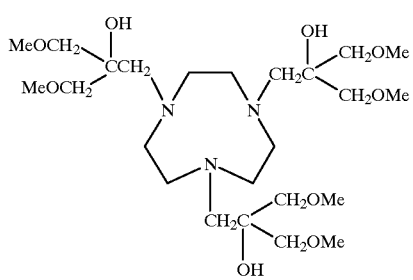

1.3.1.13 N,N',N"-Tri(2-hydroxy-(2,2-diisopropyloxymethyl)ethyl-1,4,7-triazacyclononane.

From 1,4,7-triazacyclononane (1.1.3) and 2,2-Bis-Isopropoxymethyl oxirane (1.2.2.3).

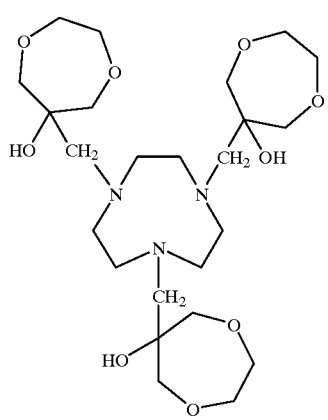

1.3.1.14 N,N',N"-Tris[2-hydroxy-bis(2-furfuryloxymethyl)ethyl]-1,4,7-triazacyclononane.

From 1,4,7-triazacynononane (1.1.3) and 2,2-Bis (furfuryloxymethyl) oxirane (1.2.2.4).

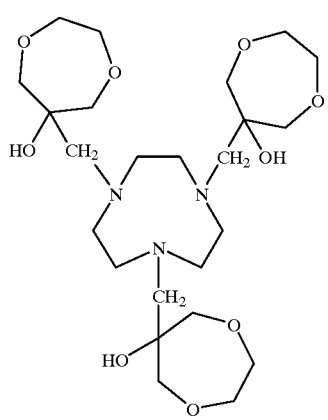

1.3.1.15 N,N',N"-Tris(3-hydroxy-1,5-dioxacycloheptyl-3-methyl)-1,4,7-triazacyclononane.

From 1,4,7-Triazacyclononane (1.1.3) and oxiranespiro-3-(1,5-dioxacycloheptane) (1.2.3.1).

1.3.1.16 N,N',N"-Tris[(3-Hydroxy-7,7-dimethyl-1,5-dioxacyclooct-3-yl)-methyl]-1,4,7-triazacyclononane.

From 1,4,7-Triazacyclononane (1.1.3) and oxiranespiro-3-(1,5-dioxa-7,7-dimethylcyclooctane) (1.2.3.2).

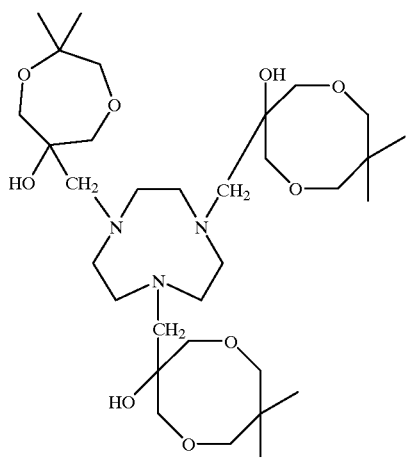

1.3.1.17 N,N',N"-Tris[(3-hydroxy-7-methyl-1,5-dioxacyclohept-3-yl)methyl]-1,4,7-triazacyclononane.

From 1,4,7-Triazacyclononane (1.1.3) and Oxiranespiro-3-(1,5-dioxa-6-methylcycloheptane(1.2.3.3).

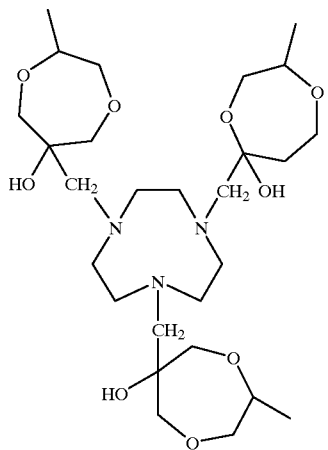

1.3.1.18 N,N',N"-Tris[(3-hydroxy-6,6,7,7-tetramethyl-1,5-dioxacyclohept-3-yl)methyl]-1,4,7-Triazacyclononane.

From 1,4,7-Triazacyclononane (1.1.3) and oxiranespiro-3-(1,5-dioxa-6,6,7,7-tetramethylcycloheptane) (1.2.3.4).

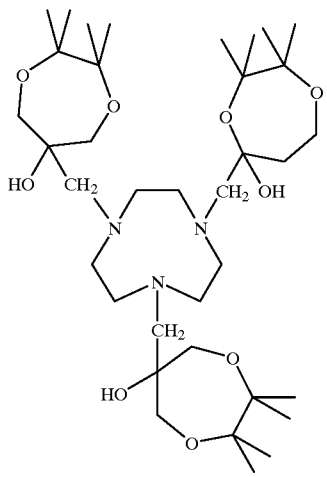

1.3.1.19 N,N',N"-Tris[(3-hydroxy-benzo[b]-1,5-dioxacycloheptyl)methyl]1,4,7-triazacyclononane.

From 1,4,7-triazacyclononane (1.1.3) and oxiranespiro-3-(benzo[b]-1,5-dioxacycloheptane) (1.2.3.5).

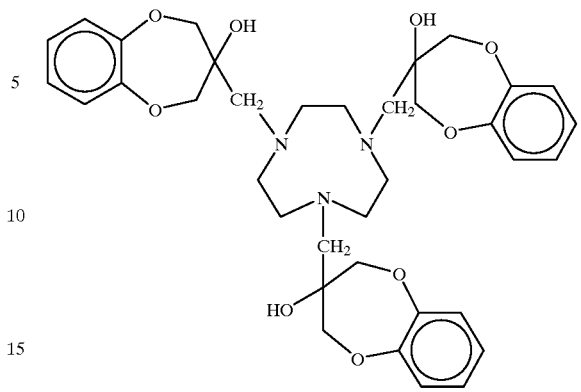

1.3.1.20 N,N',N"-Tris[(3-hydroxy-1,5-dioxacyclooctane-3-yl)methyl]-1,4,7-triazacyclononane.

From 1,4,7-triazacyclononane (1.1.3) and oxiranespiro-3-(1,5-dioxacyclooctane) (1.2.3.6).

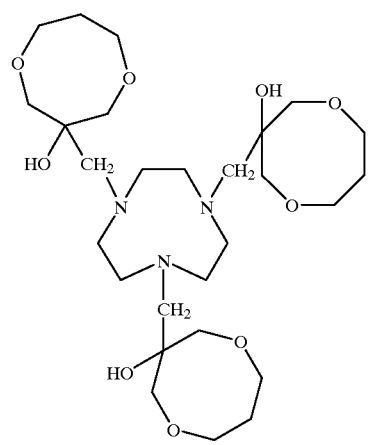

1.3.1.21 N,N',N"-Tris(2-hydroxy-2-methylpropyl)-1,4,7-Triazacyclononane.

From 1,4,7-Triazacyclononane (1.1.3) and 2,2-Dimethyl oxirane (1.2.4.1)

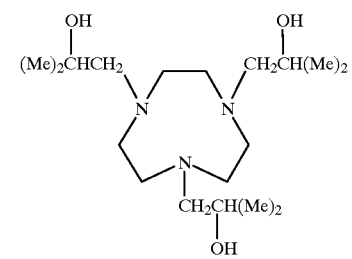

1.3.1.22 N,N',N"-Tris[(4-fluoro-2-hydroxy-3-i-propyl-4-methyl) pentyl]-1,4,7-triazacyclononane.

From 1,4,7-triazacyclononane (1.1.3) and 2-isopropyl-2-(1-fluoro-1-methylethyl) oxirane (1.2.4.2).

1.3.1.22

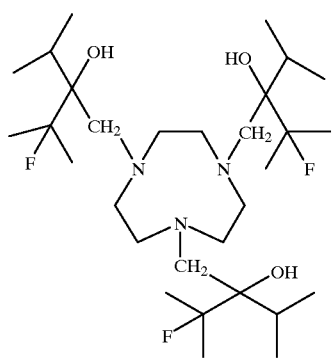

1.3.1.25

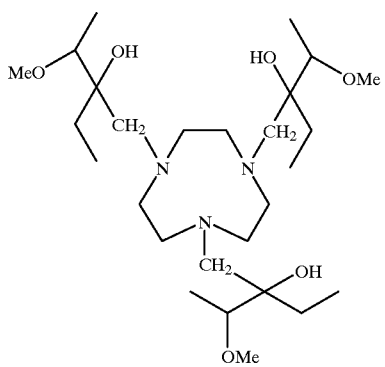

1.3.1.23 N,N',N"-Tris-[2-hydroxy-3-(1-fluoroethyl)-4-hydroxypentyl]-1,4,7-triazacyclononane.

From 1,4,7-triazacyclononane (1.1.3) and 2-(1-trimethylsilyloxyethyl)-2-(1-fluoroethyl) oxirane (1.2.4.8).

1.3.1.26 N,N', N"-Tris(2,3-dihydroxy-2-ethyl)butyl]-1,4,7-Triazacyclononane.

From 1,4,7-triazacyclononane (1.1.3) and 2-ethyl-2-(1-trimethylsilyloxyethyl) oxirane (1.2.4.28).

1.3.1.23

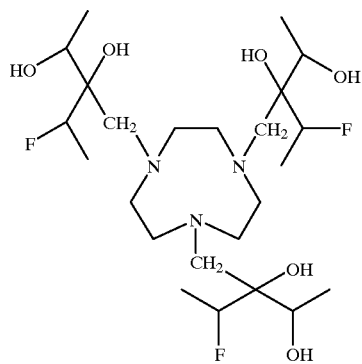

1.3.1.26

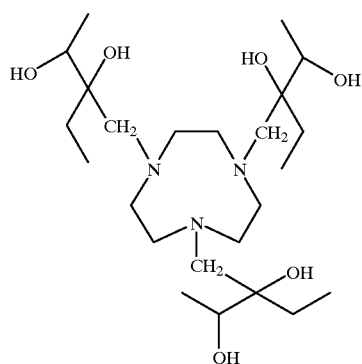

1.3.1.24 N,N',N"-Tris[2-hydroxy-2-(1-fluoroethyl)-2-(1-methoxyethyl)ethyl]-1,4,7-triazacyclononane.

From 1,4,7-triazacyclononane (1.1.3) and 2-(1-Fluoroethyl)-2-(1-methoxyethyl) oxirane (1.2.4.19).

1.3.1.27 N,N',N"-Tris[2-hydroxy-2,2-bis(1-fluoro ethyl) ethyl]-1,4,7-triazacyclononane.

From 1,4,7-triazacylononane (1.1.3) and 2,2-bis(1-fluoroethyl) oxirane (1.2.4.33).

1.3.1.24

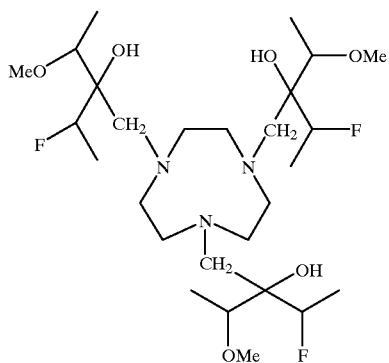

1.3.1.27

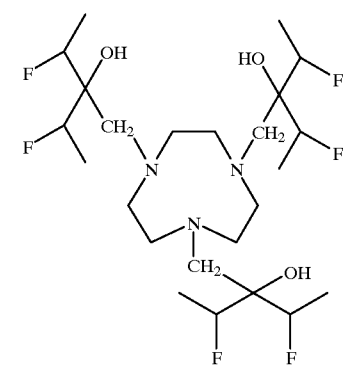

1.3.1.25 N, N',N"-Tris (2-hydroxy-2-ethyl-3-methoxy butyl)-1,4,7-triazacyclononane.

From 1,4,7-triazacyclononane (1.1.3) and 2-ethyl-2-(1-methoxyethyl) oxirane (1.2.4.24).

1.3.1.28 N,N',N"-Tris[2-hydroxy-2,2-bis(1-methoxyethyl) ethyl]-1,4,7-triazacyclononane.

From 1,4,7-Triazacyclononane (1.1.3) and 2,2-(1-methoxyethyl) oxirane (1.2.4.37).

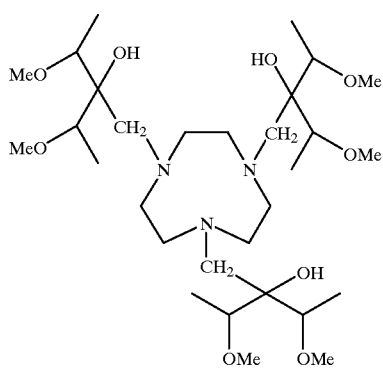

1.3.1.28

1.3.1.29 N,N',N"-Tris[(3,3-dimethyl-2-hydroxy)butyl]-1,4,7-triazacyclononane.

From 1,4,7-Triazacyclononane (1.1.3), 1-Bromo-2-hydroxy-3,3-dimethylbutane (1.2.6.1) and sodium carbonate.

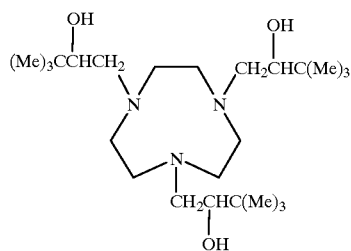

1.3.1.29

1.3.1.30 N,N',N"-Tris(2-hydroxypropyl)-1,4,7-triazacyclononane.

From 1,4,7-triazacyclononane (1.1.3) and propylene oxide.

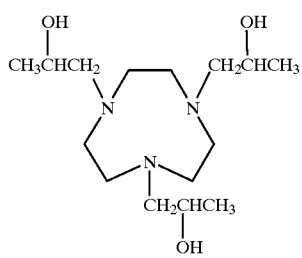

1.3.1.30

1.3.1.31 N,N',N"-Tris(2,2-dimethoxyethanyl)-1,4,7-triazacyclononane.

From 1,4,7-triazacyclononane (1.1.3), 1-chloro-2,2-dimethoxyethane (commercially available) and sodium carbonate.

1.3.1.31

1.3.1.32 N,N',N"-Tris(2-hydroxycyclopentan-1-yl)-1,4,7-triazacyclononane.

From 1,4,7-triazacyclononane (1.1.3), 1,2-epoxycyclopentane (commercially available) and sodium carbonate.

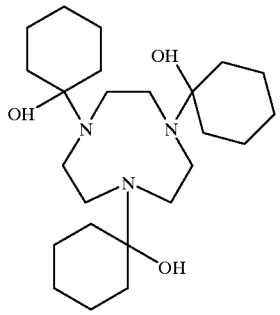

1.3.1.32

1.3.1.33 N,N',N"-Tris(2-hydroxycyclohexane-1-yl)-1,4,7-triazacyclononane.

From 1,4,7-triazacyclononane (1.1.3), 1,2-epoxycyclohexane (commercially available) and sodium carbonate.

1.3.1.33

1.3.1.34 N,N',N"-Triallyl-1,4,7-Triazacyclononane.

From 1,4,7-triazacyclononane (1.1.3), sodium hydride and allyl bromide.

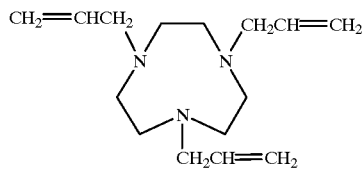

1.3.1.34

1.3.1.35 N,N',N"-Tris[(3-chloro-2-hydroxy)propyl)]-1,4,7-Triazacyclononane.

From N,N',N"-triallyl-1,4,7-triazacyclononane(1.3.1.34) and aqueous chlorine.

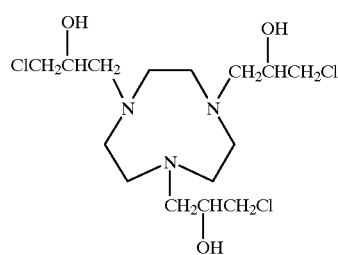
1.3.1.35

1.3.1.36 1,2-Bis-(N,N'-di-2-hydroxyethyl-1,4,7-triazacyclononane-1-yl) ethane.

From 1,2-bis-(1,4,7-triazacyclononane-1-yl) ethane polyhydrobromide and ethylene oxide.

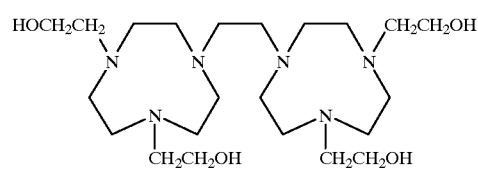
1.3.1.36

1.3.1.37 N,N',N'',N'''-Tetrakis-(2-hydroxyethyl)-1,4,7,10-tetraazacyclododecane.

From 1,4,7,10-Tetraazacyclododecane (1.1.4) and bromoethanol.

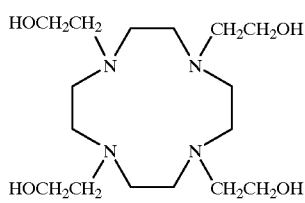
1.3.1.37

1.3.1.38 N,N',N'',N'''-Tetrakis(2,3-dihydroxypropyl)-1,4,7,10-tetraazacyclotetradecane.

From 1,4,7,10-tetraazacyclotetradecane (1.1.4), 1-chloro-2,3-propanediol (commercially available) and base.

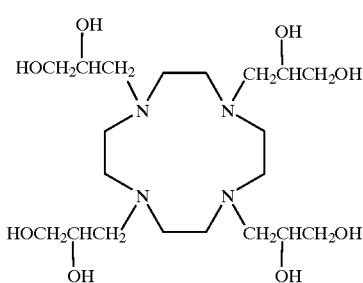
1.3.1.38

1.3.1.39 4,10-Bis(2-Hydroxypropyl)-1,4,7,10-tetraazabicyclo [5.5.2]tetradecane.

From 1,4,7,10-tetraazabicyclo[5.5.2]tetradecane (1.1.4) and propylene oxide.

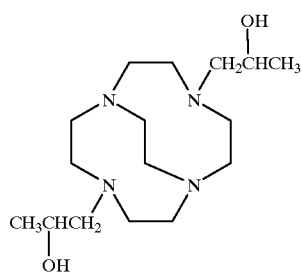
1.3.1.39

1.3.1.40 4,10-Bis-(2-hydroxyethyl)-1,4,7,10-tetraazabicyclo [5.5.2]tetradecane.

From 4,10-Bis(dimethoxycarbonylmethyl)-1,4,7,10-tetraazabicyclo[5.5.2] tetradecane (1.3.6.8) and lithium aluminum hydride.

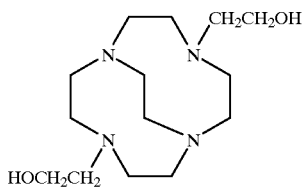
1.3.1.40

1.3.1.41 4,10-Bis[(2-Hydroxy-2-phenyl)ethyl]-1,4,7,10-tetraazabicyclo[5.5.2]tetradecane.

From 1,4,7,10-Tetraazabicyclo[5.5.2]tetradecane (1.1.4) and styrene oxide.

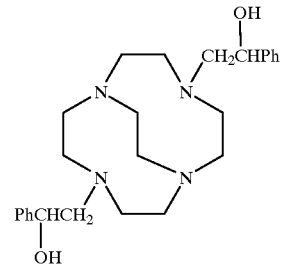
1.3.1.41

1.3.1.42 4,10-Bis-(2,3-dihydroxypropyl)-1,4,7,10-tetraazabicyclo [5.5.2]tetradecane.

From 1,4,7,10-tetraazabicyclo[5.5.2]tetradecane (1.1.4) and glycidol.

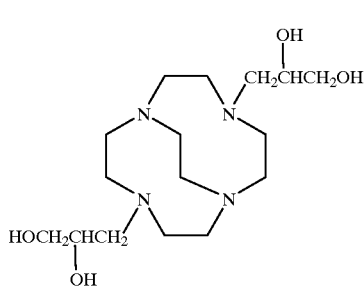
1.3.1.42

1.3.1.43 N,N',N'',N'''-Tetrakis-(2,3-dihydroxypropyl)-1,4,8,11-tetraazacyclohexadecane.

From cyclam (1.1.5) and glycidol.

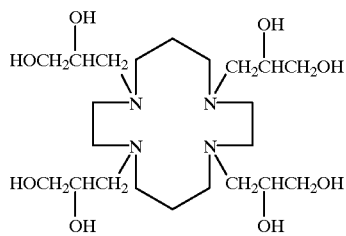

1.3.1.44 cis, trans N,N,N',N'-Tetrakis(2,3-dihydroxypropyl)-1,2-diamino-cyclohexane.

From cis,trans 1,2-diaminocyclohexane (commercially available) and glycidol.

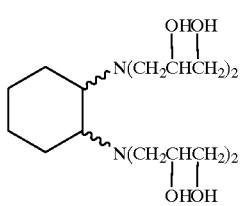

1.3.1.45 trans N,N,N',N'-Tetrakis(2,3-dihydroxypropyl)-1,2-diamino-cyclohexane.

From trans-1,2-diaminocyclohexane (commercially available) and glycidol.

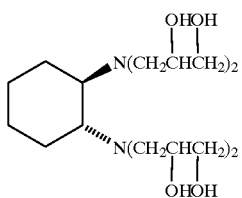

1.3.1.46 N,N,N',N'-Tetrakis(2,3-dihydroxypropyl)-ethylenediamine.

From ethylenediamine (1.1.0) and glycidol.

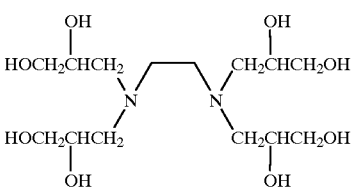

1.3.1.47 N,N,N',N'',N'''-Pentakis(2,3-dihydroxypropyl)-diethylenetriamine.

From diethylenetriamine (1.1.1), 1-chloro-2,3-propanediol and base.

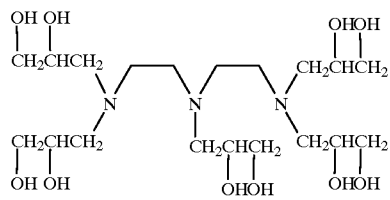

1.3.1.48 N,N,N',N'',N''',N'''-Hexaakis(2,3-dihydroxypropyl) triethylenetetramine.

From triethylenetetramine (1.1.2) and glycidol.

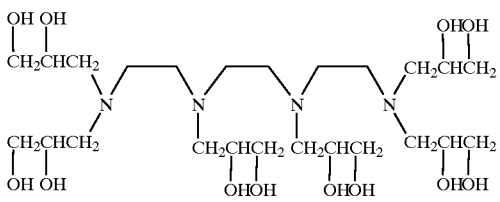

1.3.1.49 N,N,N',N'-Tetrakis(2,3-dihydroxypropyl)-1,2-diamino-2-methylpropane.

From 1,2-diaminomethylpropane and glycidol.

1.3.1.50 N,N,N',N'-Tetrakis(2,3-dihydroxypropyl)-1,2-diaminopropane.

From 1,2-diaminopropane and glycidol.

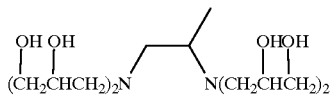

1.3.1.51 N,N',N''-Tris(2,3-diacetoxypropyl)-1,4,7-triazacyclononane.

From 1.3.1.7 and Py/Ac$_2$O.

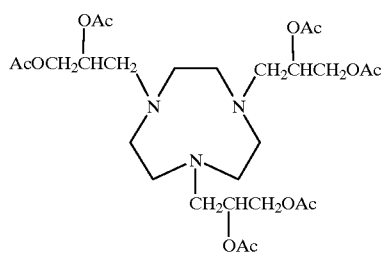

1.3.1.52 N,N',N''-tris(Dimethyl-2,3-isopropylidene propyl)-1,4,7-triazacyclononane.

From 1.3.1.7 and 2,2-dimethoxypropane/p-toluenesulfonic acid.

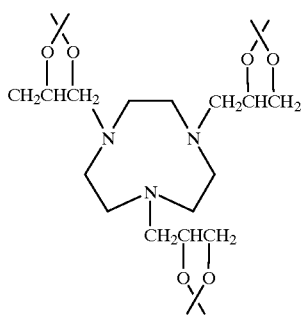

1.3.1.53 4,10-(2-Diacetoxyoxypropyl)-1,4,7,10-tetraazabicyclo [5.5.2]tetradecane.

From 1.3.1.39 and Py/Ac₂O.

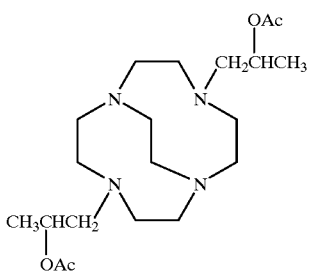

1.3.1.54 N,N',N"-Tris[(2,4-dihydroxy-3-isopropyl-4-methyl)pentyl]-1,4,7-triazacyclononane.

From 1,4,7-triazacyclononane (1.1.3) and 2,2-bis(hydroxymethyl) oxirane.

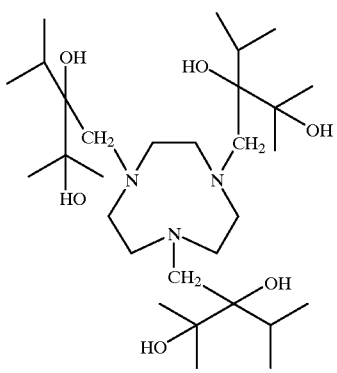

1.3.1.55 N,N',N"-Tris-[2-hydroxy-(2,2-dihydroxymethyl)ethyl]-1,4,7-triazacyclononane.

From 1,4,7-triazacyclononane (1.1.3) and 2,2-bis(hydroxymethyl) oxirane (1.2.2.5).

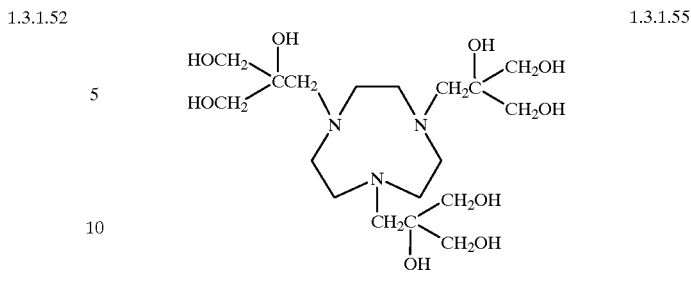

1.3.2 Synthesis of Polyaza Ligands With Alkylphosphonate Mono- and Di-Esters Pendant Arms.

1.3.2.1 Preparation

Chelators which have three identical methylene phosphonate diester arms were prepared by reacting the trihydrobromide polyaza bases with formaldehyde and dialkylphosphite. The hexa-ester was hydrolized to the tri-ester by heating with NaOH dissolved in the appropriate alcohol (the same R group as in the dialkylphosphite). In some cases products were obtained by reacting the amine base with haloalkylphosphonates or epoxyphosphonates.

1.3.2.1 N,N',N"-Tris(dibutylphosphorylmethyl)-1,4,7-triazacyclononane.

From 1,4,7-triazacyclononane (1.1.3) trihydrobromide, formaldehyde solution and di-n-butyl phosphite (1.2.5.1).

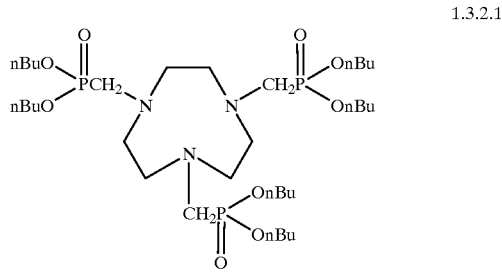

1.3.2.2 N,N',N"-Tris(dihydroxyphosphorylmethyl mono butyl ester)-1,4,7-triazacyclononane.

From N,N',N"-tris(dibutylphosphorylmethyl)-1,4,7-triazacyclononane (1.3.2.1) and KOH/butanol.

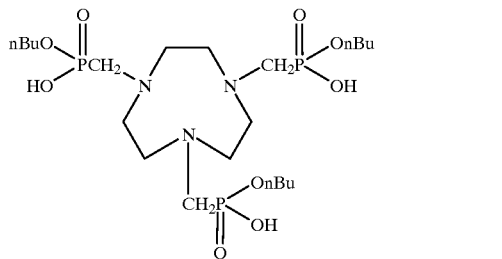

1.3.2.3 N,N',N"-Tris(diethylphosphorylmethyl)-1,4,7-triazacyclononane.

From 1,4,7-triazacyclononane (1.1.3) trihydrobromide, formaldehyde solution and diethyl phosphite (commercially available).

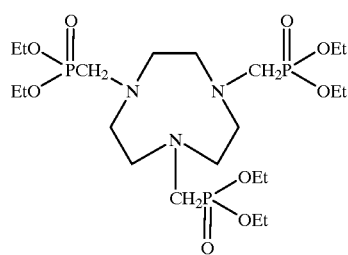

1.3.2.3

1.3.2.4 N,N',N''-Tris(dihydroxyphosphorylmethyl monoethyl ester)-1,4,7-triazacyclononane.
From N,N',N''-tris(diethylphosphorylmethyl)-1,4,7-triazacyclononane (1.3.2.3) and NaOH/EtOH.

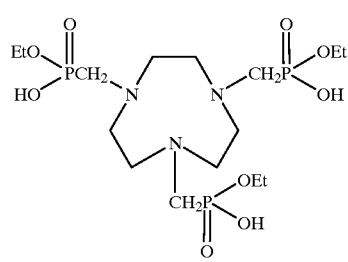

1.3.2.4

1.3.2.5 N,N',N''-Tris(dioctylphosphorylmethyl)-1,4,7-triazacyclononane.
From 1,4,7-triazacyclononane (1.1.3), formaldehyde and dioctylphosphite (1.2.5.2).

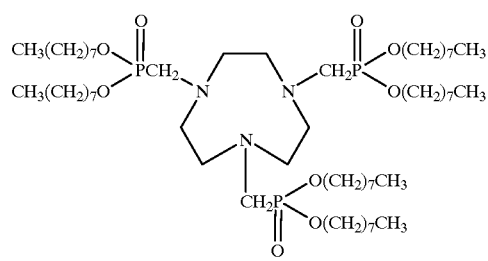

1.3.2.5

1.3.2.6 N,N',N''-Tris(dihydroxyphosphorylmethyl monooctyl ester)-1,4,7-triazacyclononane.
From 1.3.2.5 and NaOH in octyl alcohol.

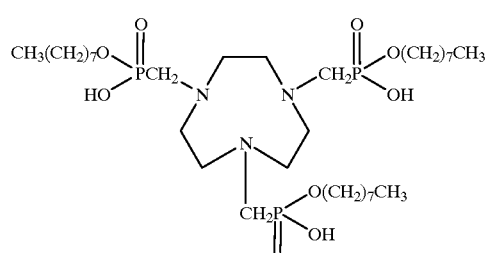

1.3.2.6

1.3.2.7 N,N',N''-Tris(diisobutylphosphorylmethyl)-1,4,7-triazacyclononane.
From 1,4,7-Triazacyclononane (1.1.3), formaldehyde and diisobutylphosphite (1.2.5.3).

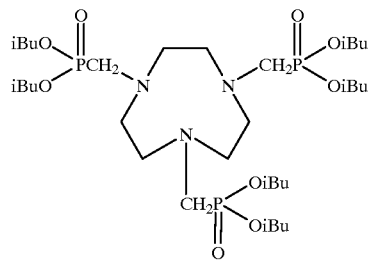

1.3.2.7

1.3.2.8 N,N',N''-Tris(dihydroxyphosphorylmethyl monoisobutyl ester)-1,4,7-triazacyclononane.
From 1.3.2.7 and NaOH in isobutyl alcohol.

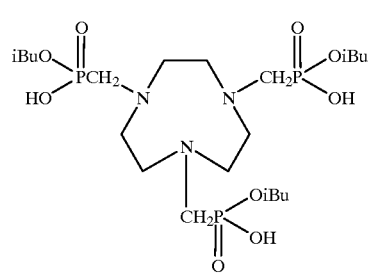

1.3.2.8

1.3.2.9 N,N',N''-Tris(dibenzylphosphorylmethyl)-1,4,7-triazacyclononane.
From 1,4,7-Triazacyclononane (1.1.3), formaldehyde and dibenzylphosphite (1.2.5.4).

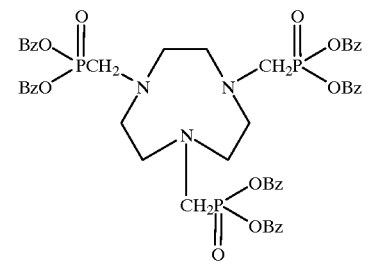

1.3.2.9

1.3.2.10 N,N',N''-Tris(diethylphosphorylethyl)-1,4,7-triazacyclononane.
From 1,4,7-triazacyclononane (1.1.3) trihydrobromide, potassium carbonate and diethyl(2-bromoethyl)phosphonate (1.2.5.5).

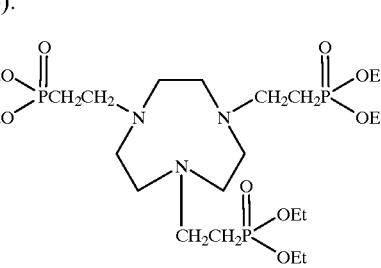

1.3.2.10

1.3.2.11 N,N',N'',N'''-Tetrakis(diethylphosphorylmethyl)-1,4,7,10-Tetraazacyclodecane.
From 1,4,7,10-Tetraazacyclodecane (1.1.4) trihydrobromide, formaldehyde and diethylphosphite (commercially available).

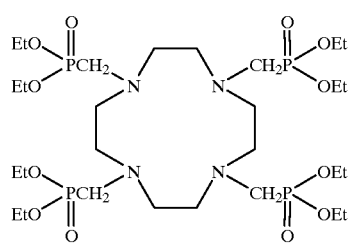

1.3.2.11

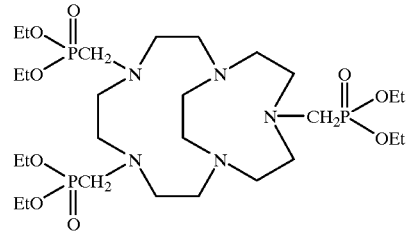

1.3.2.15

1.3.2.12 N,N',N'',N'''-Tetrakis(diethylphosphorylethyl)-1,4,7,10-tetraazacyclododecane.

From 1,4,7,10-tetraazacyclododecane (1.1.4) trihydrobromide, potassium carbonate and diethyl(2-bromoethyl)phosphonate (1.2.5.5).

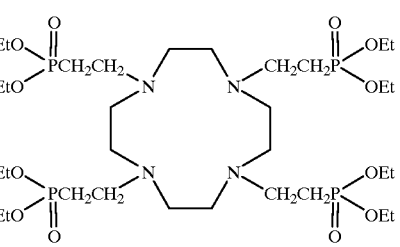

1.3.2.12

1.3.2.13 4,10-Bis(diethylyphosphorylethyl)-1,4,7,10-tetraazabicyclo [5.5.2]tetradecane.

From 1,4,7,10-tetraazabicyclo[5.5.2]tetradecane (1.1.20) dihydrobromide, potassium carbonate and diethyl(2-bromoethyl)phosphonate (1.2.5.5).

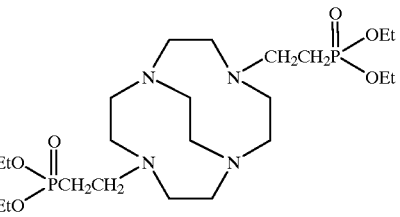

1.3.2.13

1.3.2.14 4,10-Bis(diethylphosphoryl methyl)-1,4,7,10-tetraazabicyclo [5.5.2]tetradecane.

From 1,4,7,10-tetraazabicyclo[5.5.2]tetradecane (1.1.20) trihydrobromide, formaldehyde and diethyiphosphite (commercially available).

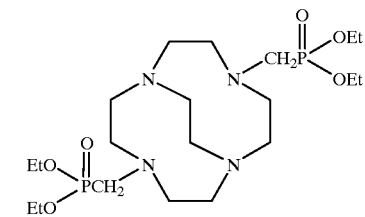

1.3.2.14

1.3.2.15 N,N',N''-Tris(diethylphosphorylmethyl)-1,4,7,10,13-pentaazabicyclo [8.5.2]heptadecane.

From 1,4,7,10,13-pentaazabicyclo[8.5.2]heptadecane (1.1.25), formaldehyde and diethylphosphite (commercially available).

1.3.3 Synthesis of Polyaza Ligands with Identical Alkylphosphonic Acid Pendant Arms.

These compounds were prepared by either hydrolizing the ester groups of the compounds described under 1.3.2, or from the polyaza base, formaldehyde and phosphorous acid.

1.3.3.1 1,2-Bis(N,N'-bis(dihydroxyphosphrylmethyl)-1,4,7-triazacyclononan-1-yl) ethane.

From 1,2-bis-(1,4,7-triazacyclononan-1-yl)ethane (1.1.28), formaldehyde and phosphorous acid.

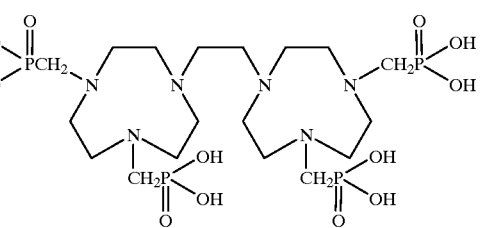

1.3.3.1

1.3.3.2 1,2-Bis(N,N'-bis(dihydroxyphosphorylmethyl)-1,4,7-triazacyclononan-1-yl)propane.

From 1,2-Bis-(1,4,7-triazacyclononan-1-yl)propane (1.1.19), formaldehyde and phosphorous acid.

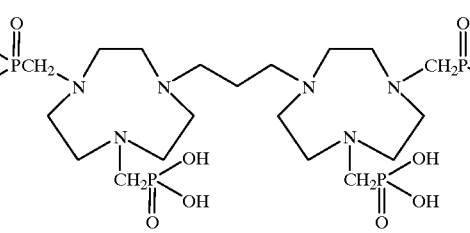

1.3.3.2

1.3.3.3 4,10-Bis(dihydroxyphosphorylmethyl)-1,4,7,10-tetraazabicyclo[5.5.2]tetradecane.

From 1,4,7,10-Tetraazabicyclo[5.5.2]tetradecane (1.1.20) trihydrobromide, formaldehyde and phosphorous acid.

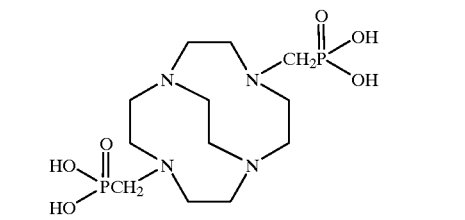

1.3.3.3

1.3.3.4 4,7,13-Tris(dihydroxyphosphorylmethyl)-1,4,7,10,13-pentaazabicyclo[8.5.2]heptadecane.

From hydrolysis of 1,4,7,13-tris(diethylphosphorylmethyl)-1,4,7,10,13-pentaazabicyclo[8.5.2]heptadecane (1.3.2.15) by HCl.

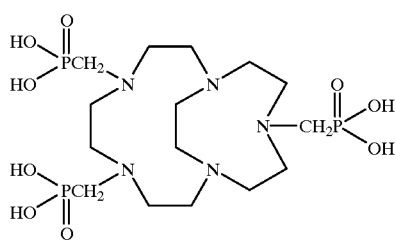

1.3.3.4

The following compounds were prepared from the corresponding diesters by hydrolysis with HCl:

1.3.3.5 N,N',N"-Tris(dihydroxyphosphorylethyl)-1,4,7-triazacyclononane.

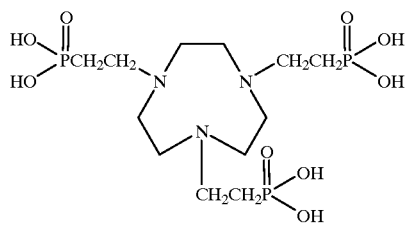

1.3.3.5

1.3.3.6 N,N',N",N'"-Tetrakis(dihydroxyphosphorylethyl)-1,4,7,10-tetraazacyclododecane.

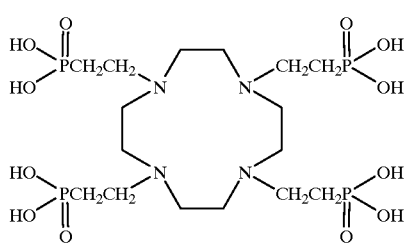

1.3.3.6

1.3.3.7 4,10-Bis(dihydroxyphosphorylethyl)-1,4,7,10-tetraazabicyclo[5.5.2]tetradecane.

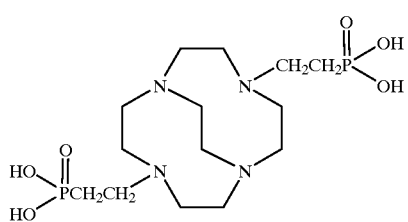

1.3.3.7

1.3.4 Synthesis of Polyaza Ligands with Pendant Arms Containing Phosphonate Esters and Acids with Alpha Substituent Groups.

Alkyl or aryl groups α to the phosphonate moiety were prepared by alkylation of the corresponding ligand in the form of its dialkylphosphonate.

1.3.4.1 N,N',N"-Tris[α-dihydroxyphosporyl-α-benzyl)methyl]-1,4,7-Triazacyclononane.

From N,N',N"-Tris[(α-diethylphosporyl-α-benzyl)methyl]-1,4,7-triazacyclononane (U.S. Pat. No. 5,380,515) and trimethylsilyl iodide.

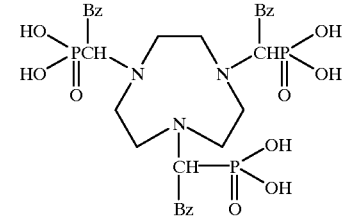

1.3.4.1

1.3.4.2 N,N',N"-Tris{[(diethylphosphoryl)-α-hydroxy]ethyl}-1,4,7-triazacyclononane.

From 1,4,7-triazacyclononane (1.1.3) and 2-diethylphosphoryl oxirane (1.2.5.7).

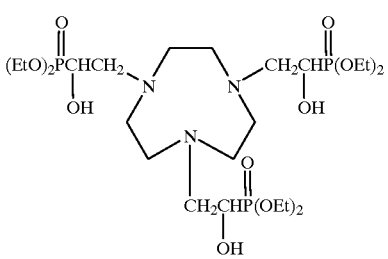

1.3.4.2

1.3.4.3 N,N',N"-Tris[dihydroxyphosphoryl-α-hydroxy)ethyl]-1,4,7-triazacyclononane.

From 1.3.4.2 and HCl.

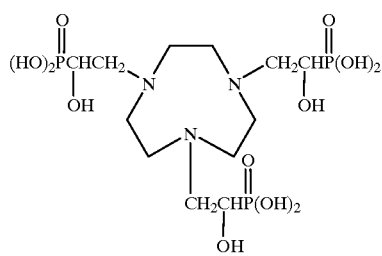

1.3.4.3

1.3.5 Synthesis of Polyaza Ligands with Pendant Arms Containing Hydroxamate Groups.

These compounds were prepared by reacting 1,4,7-tetraazacyclononane (1.1.3) trihydrobromide with a N-alkyl-O-benzyl chloroacetohydroxamic acid in the presence of a base. The free hydroxamic acid was obtained by removing the benzyl protecting group by hydrogenolysis.

1.3.5.1 N,N',N"-Tris[(N-methyl-N-benzyloxycarbamoyl)methyl]1,4,7-triazacyclononane.

From 1,4,7-triazacyclononane, sodium carbonate and O-benzyl-N-methyl chloroacetohydroxamate (1.2.7.1).

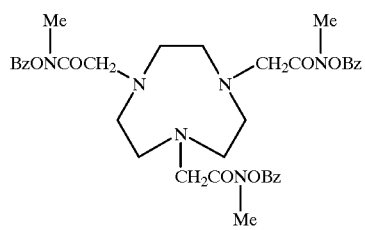

1.3.5.2 N,N',N"-Tris[(N-methyl-N-hydroxycarbamoyl)methyl]-1,4,7-triazacyclononane.

From N,N',N"-Tris[(N-methyl-N-benzyloxycarbamoyl)methyl]-1,4,7-triazacyclononane (1.3.5.1) and H₂ and Pd/C.

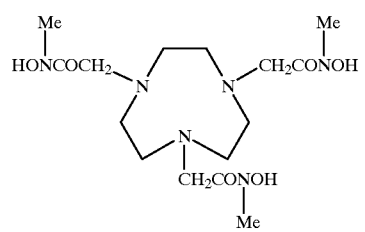

1.3.5.3 N,N',N"-Tris[(N-isopropyl-N-benzyloxycarbamoyl)methyl]-1,4,7-triazacyclononane.

From 1,4,7-Triazacyclononane trihydrobromide and chloroaceto-N-isopropyl-O-benzyl hydroxamate (1.2.7.2).

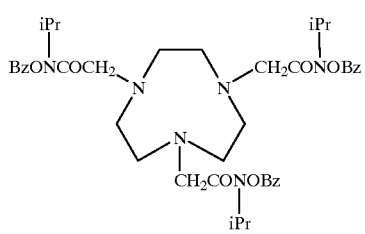

1.3.5.4 N,N',N"-Tris[(N-isopropyl-N-hydroxycarbamoyl)methyl]-1,4,7-triazacyclononane.

From 1.3.5.3 and H₂ and Pd/C.

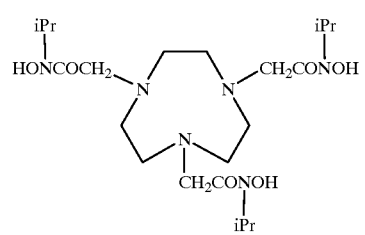

1.3.5.5 N,N',N"-Tris[(N-t-butyl-N-benzyloxycarbamoyl)methyl]-1,4,7-triazacyclononane.

From 1,4,7-triazacyclononane trihydrobromide and chloroaceto-N-t-butyl-O-benzyl hydroxamate (1.2.7.3).

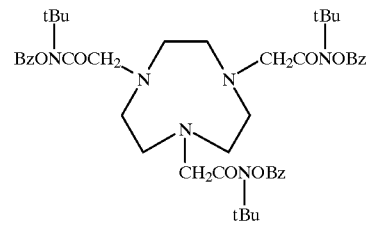

1.3.5.6 N,N',N"-Tris((N-t-butyl-N-hydroxycarbamoyl)methyl]-1,4,7-triazacyclononane.

From 1.3.5.5, H₂ and Pd/C.

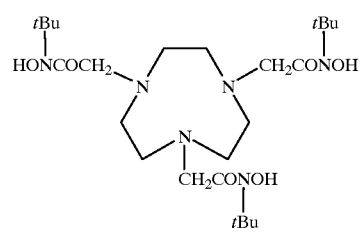

1.3.5.7 N,N',N"-Tris[(N-benzyloxycarbamoyl)methyl]-1,4,7-triazacyclononane.

From 1,4,7-triazacyclononane (1.1.3) trihydrobromide and chloroaceto-O-benzyl hydroxamate (1.2.7.4).

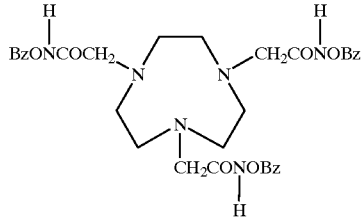

1.3.5.8 N,N',N"-Tris[(N-hydroxycarbamoyl)methyl]-1,4,7-triazacyclononane.

From 1.3.5.7 and H₂ and Pd/C.

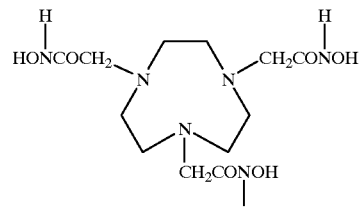

1.3.5.9 N,N',N"-Tris[(N-methoxycarbamoyl)methyl]-1,4,7-triazacyclononane.

From 1,4,7-triazacyclononane (1.1.3) trihydrobromide and chloroaceto-O-methyl hydroxamate (1.2.7.5).

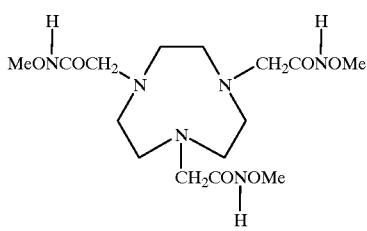

1.3.5.9

1.3.5.10 4,10-Bis[(N-benzyloxycarbamoyl-N-methyl)methyl]-1,4,7,10-tetraazabicyclo[5.5.2]tetradecane.

From 1,4,7,10-tetraazabicyclo[5.5.2]tetradecane (1.1.20) dihydrobromic acid, sodium carbonate and chloroaceto-O-benzyl hydroxamate (1.2.7.4).

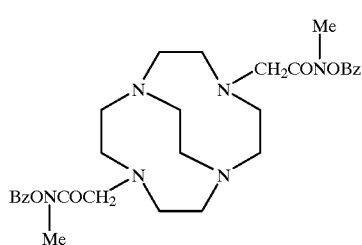

1.3.5.10

1.3.5.11 4,10-Bis[(N-hydroxycarbamoyl-N-methyl)methyl]-1,4,7,10-Tetraazabicyclo [5.5.2] tetradecane.

From 1.3.5.10 and $H_2$ and Pd/C.

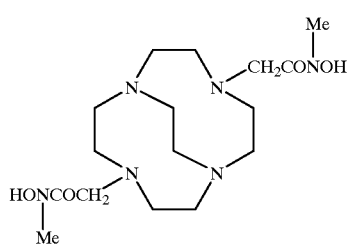

1.3.5.11

1.3.5.12 N,N',N"-Tris[(1-benzyloxy-2-pyrrolidone-5-yl)methyl]-1,4,7-triazacyclononane.

From 1,4,7-triazacyclononane (1.1.3), 5-(p-toluenesulfonyloxymethyl)-1-benzyloxy-2-pyrrolidone (1.2.6.3) and base.

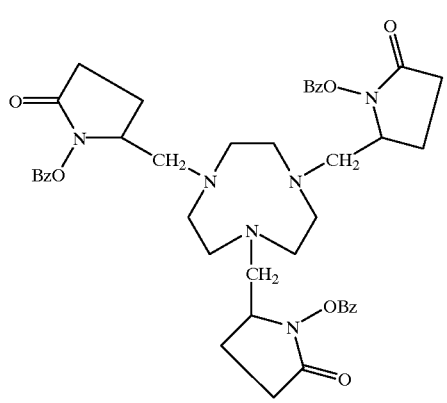

1.3.5.12

1.3.5.13 N,N',N"-Tris[(1-oxy-2-pyrrolidone-5-yl)methyl]-1,4,7-triazacyclononane.

From 1.3.5.12 and Pd/C (5%) and $H_2$.

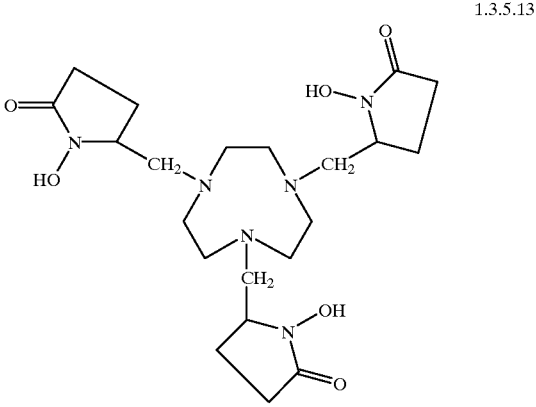

1.3.5.13

1.3.5.14 N,N',N"-Tris(1-benzyoxy-2-pyrrolidone-5-yl)-1,4,7-triazacyclononane.

From 1,4,7-triazacyclononane (1.1.3), 5-bromo-1-benzyloxy-2-pyrrolidone (1.2.6.11) and base.

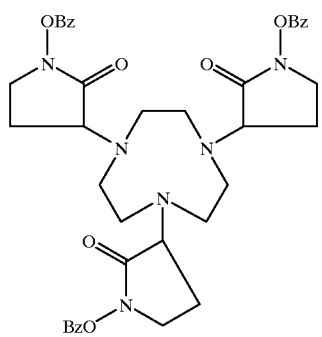

1.3.5.14

1.3.5.15 N,N',N"-Tris(1-oxy-2-pyrrolidone-5-yl)-1,4,7-triazacyclononane.

From 1.3.5.14 and Pd/C (5%) and $H_2$.

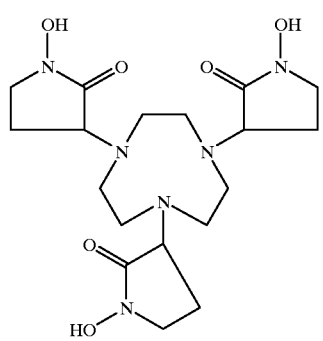

1.3.5.15

1.3.6 Synthesis of Polyaza Ligands with Pendant Arms Containing Carboxyl Groups And The Corresponding Esters.

Compounds were prepared by reacting polyaza bases with either halo carboxylic acids or by reductive alkylation with aldo or keto acids. The esters were prepared either by reacting directly with halo carboxylic acid esters or by reaction of the free acid with $SOCl_2$/alcohol.

1.3.6.1 N,N',N"-Tris(carboxymethyl)-1,4,7-triazacyclononane.

From 1,4,7-triazacyclononane (1.1.3), glyoxylic acid and $H_2$/Pt.

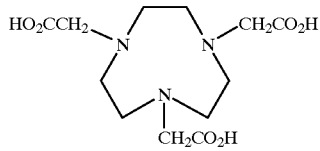

1.3.6.2 N,N',N"-Tris(methoxycarbonylmethyl-1,4,7-triazacyclononane.

From N,N',N"-tris(carboxymethyl)-1,4,7-triazacyclononane in methanol and $SOCl_2$.

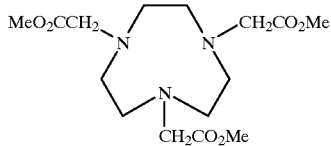

1.3.6.3 N,N',N"-Tris(α-methylcarboxymethyl)-1,4,7-Triazacyclononane.

From 1,4,7-triazacyclononane (1.1.3), pyruvic acid and $H_2$/Pt.

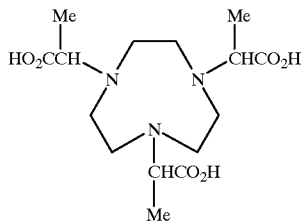

1.3.6.4 N,N',N"-Tris(methoxycarbonylmethyl-1,4,7-triazabicyclo-[7.4.0$^{8,13}$]tridecane.

From 1,4,7-Triazabicyclo[7.4.0$^{8,13}$]tridecane hydrobromide (1.1.1.4), glyoxylic acid and $H_2$/$PtO_2$ in methanol.

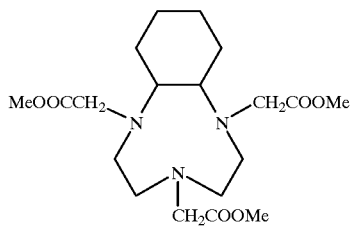

1.3.6.5 N-(α-methylcarboxymethyl)-1,4,7-triazabicyclo[7.4.0]tridecane.

From 1,4,7-triazabicyclo[7.4.0$^{8,13}$]tridecane (1.1.4), pyruvic acid and $H_2$/$PtO_2$.

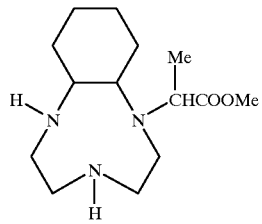

1.3.6.6 N,N',N"-Tris(ethoxycarbonylmethyl)-1,4,7-triazacyclo[7.4.0]tridecane.

From 1,4,7-triazabicyclo[7.4.0$^{8,13}$]tridecane (1.1.14), sodium methoxide and ethyl bromoacetate.

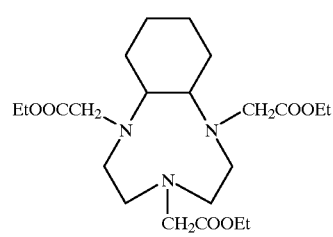

1.3.6.7 1,2-Bis-(4,7-carboxymethyl-1,4,7-triazacyclononan-1-yl)ethane.

From 1,2-Bis(1,4,7-triazacyclononan-1-yl)ethane (1.1.28), chloroacetic acid and NaOH.

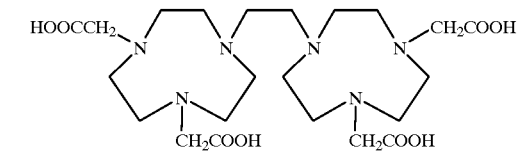

1.3.6.8 4,7-Bis(carboxymethyl)-1,4,7,10-tetraazabicyclo[5.5.2]tetradecane.

From 1,4,7,10-tetraazabicyclo[5.5.2]tetradecane (1.1.22), chloroacetic acid and NaOH.

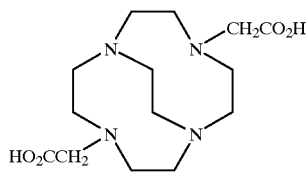

1.3.6.9 4,7-Bis(methoxycarboxymethyl)-1,4,7,10-tetraazabicyclo[5.5.2]tetradecane.

From 4,7-bis(carboxymethyl)-1,4,7,10-tetraazabicyclo[5.5.2]tetradecane (1.1.20) in MeOH/$H_2SO_4$.

1.3.6.10 N,N',N''-Tris(carboxyethyl)-1,4,7-triazacyclononane.

From 1,4,7-triazacyclononane (1.1.3), 3-chloropropionic acid and base.

1.3.6.11 4,10-Bis(ethoxycarboxymethyl)-1,4,7,10-tetraazabicyclo[5.5.2]tetradecane.

From 1,4,7,10-tetraazabicyclo[5.5.2]tetradecane (1.1.20) and ethyl acrylate.

1.3.6.12 4,10-Bis(carboxymethyl)-1,4,7,10-tetraazabicyclo[5.5.2]tetradecane.

From 1.3.6.11 by acid hydrolysis.

1.3.6.13 N,N',N''-Tris(ethoxycarbonylmethyl)-1,4,7-triazacyclononane.

From 1,4,7-triazacyclononane (1.1.3), ethyl bromoacetate and base.

1.3.6.14 1,2-Bis-(4,7-methoxycarbonylmethyl-1,4,7-triazacyclononan-1-yl)-ethane.

From 1,2-bis-(4,7-carboxymethyl-1,4,7-Triazacyclononan-1-yl)ethane (1.3.6.7), MeOH/SOCl$_2$.

1.3.7 Synthesis of Polyaza Ligands with Pendant Arms Containing Aldehyde or Ketone Groups.

1.3.7.1 N,N',N''-Tris(2,2-dimethoxyethyl)-1,4,7-triazacyclononane.

From 1,4,7-triazacyclononane (1.1.3), 1-chloro-2,2-dimethoxyethane (commercially available) and sodium carbonate.

1.3.7.2 N,N',N''-Tris-(3,3-dimethyl-2-oxo-butyl)-1,4,7-triazacyclononane.

From 1,4,7-triazacyclononane (1.1.3), bromomethyl t-butyl ketone (commercially available) and sodium carbonate.

1.3.8 SYNTHESIS OF POLYAZA LIGANDS WITH PENDANT ARMS CONTAINING PYRROLE GROUPS.

1.3.8.1 N,N',N''-Tris(-pyrrol-2-yl-methyl)-1,4,7-triazacyclononane.

From 1,4,7-triazacyclononane (1.1.3), pyrrole-2-carboxaldehyde (commercially available) and H$_2$/PtO$_2$.

1.3.9 SYNTHESIS OF POLYAZA LIGANDS WITH PENDANT ARMS CONTAINING AMINE GROUPS.

1.3.9.1 N,N',N''-Tris(2-p-toluenesulfonyloxyethyl)-1,4,7-triazacyclononane.

From 1,4,7-triazacyclononane (1.1.3), 2-(p-toluenesulfonylamino)-1-(p-toluenesulfonyloxy)ethane (1.1.16) and base.

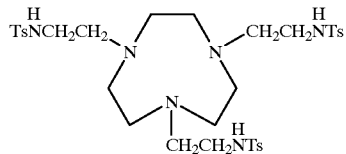

1.3.9.1

1.3.9.2 N,N',N"-Tris(2-aminoethyl)-1,4,7-triazacyclononane.
From 1.3.9.1 and HBr/acetic acid.

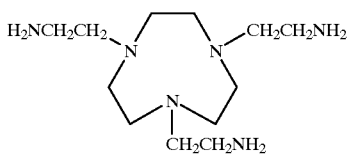

1.3.9.2

1.3.10 Synthesis of Polyaza Ligands with Pendant Arms Containing Amide Groups.
1.3.10.1 N,N',N"-Tris(methylcarbox amide)-1,4,7-triazacyclononane.
From N,N'N"-Tris-(methoxycarboxymethyl)-1,4,7-triazacyclononane (1.3.6.2) and ammonia.

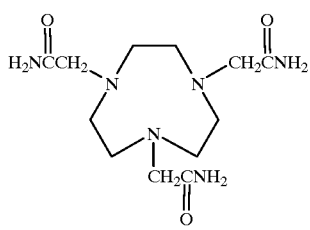

1.3.10.1

1.3.10.2 N,N',N"-Tris[-N-n-butyl(methylcarboxamide)]-1,4,7-triazacyclononane.
From N,N',N"-Tris-(methoxycarboxymethyl)-1,4,7-triazacyclononane (1.3.6.2) and butylamine.

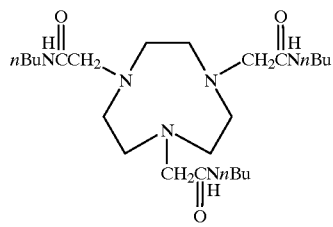

1.3.10.2

1.3.10.3 N,N',N"-Tris[-N-n-phenyl(methylcarboxamide)]-1,4,7-triazacyclononane.
From 1,4,7-triazacyclononane (1.1.3), N-phenylchloroacetamide (prepared from aniline and chloroacetyl chloride) and excess sodium carbonate.

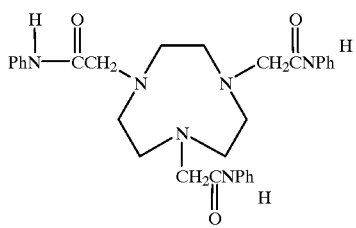

1.3.10.3

1.3.11 Synthesis of Polyaza Ligands with Pendant Arms Containing Phenolic Groups.
1.3.11.1 4,7-Di-(2-hydroxy-benzyl)-1,4,7,10-tetraazabicyclo[5.5.2]tetradecane.
From 1,4,7,10-tetraazabicyclo[5.5.2]tetradecane (1.1.20), salicylaldehyde (excess) and $H_2/PtO_2$.

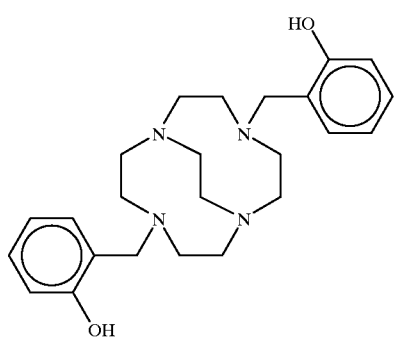

1.3.11.1

1.3.11.2 4-(2-hydroxy-benzyl)-1,4,7,10-tetraazabicyclo[5.5.2]tetradecane.
From 1,4,7,10-tetrazabicyclo[5.5.2]tetradecane (1.1.20), salicylaldehyde (1.5 equivalents) and $H_2/PtO_2$.

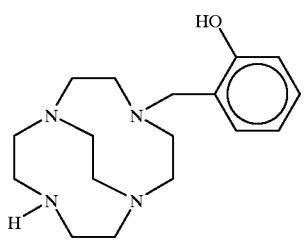

1.3.11.2

1.3.11.3 Bis-(2,2'-dihydroxybiphenylmethylene) ethylene diamine.
From ethylenediamine (1.1.0) and 2,2'-dihydroxy benzophenone (commercially available) with removal of $H_2O$.

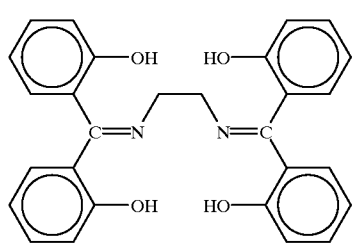

1.3.11.3

1.3.11.4 N,N'-Bis-(2,2'-dihydroxybiphenylmethyl) ethylene diamine.

From 1.3.11.3 and sodium borohydride.

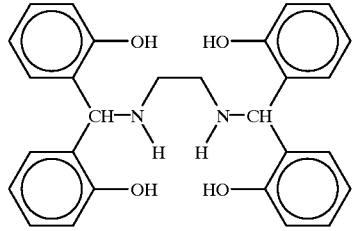

1.3.11.4

1.3.11.5 Bis-(2,4-dihydroxybiphenylmethylene) ethylenediamine.

From ethylenediamine (1.1.0) and 2,4-dihydroxy benzophenone (commercially available) with removal of $H_2O$.

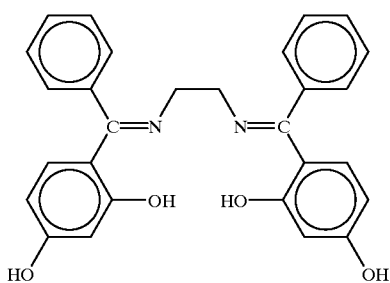

1.3.11.5

1.3.11.6 N,N'-Bis-(2,4-dihydroxybiphenylmethyl) ethylenediamine.

From 1.3.11.5 and sodium borohydride.

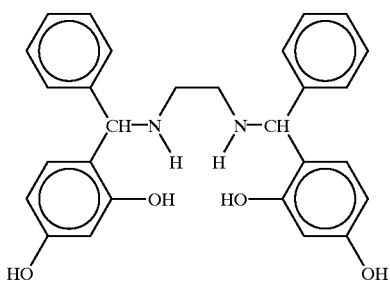

1.3.11.6

1.3.11.7 N,N"-Bis-(2,2'-dihydroxybiphenylmethylene) diethylene triamine.

From diethylene triamine (1.1.1) and 2,2'-dihydroxy benzophenone with removal of $H_2O$.

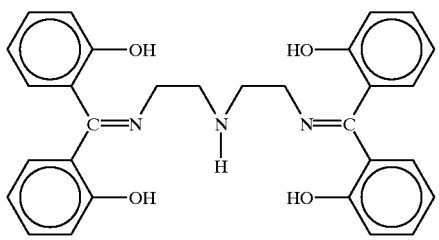

1.3.11.7

1.3.11.8 N,N"-Bis-(2,2'-dihydroxybiphenylmethyl) diethylene triamine.

From 1.3.11.7 and sodium borohydride.

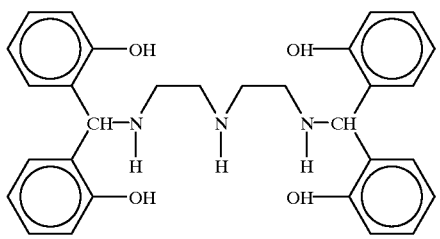

1.3.11.8

1.3.11.9 Bis-(2,2'-dihydroxybiphenylmethyiene)-1,3-diaminopropane.

From diaminopropane and 2,2'-dihydroxy benzophenone with removal of $H_2O$.

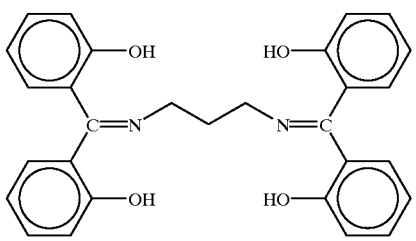

1.3.11.9

1.3.11.10 N,N'-Bis-(2,2'-dihydroxybiphenylmethyl)-1,3-diaminopropane.

From and 1.3.11.9 and sodium borohydride.

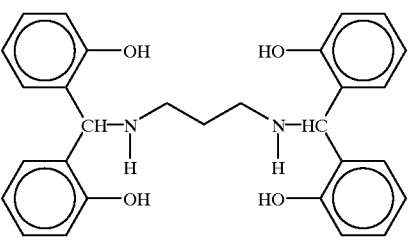

1.3.11.10

1.3.11.11 N,N',N"-Tris(2-hydroxybenzyl)-1,4,7-triazacyclononane.

From 1,4,7-triazacyclononane, salicylaldehyde and $H_2/PtO_2$.

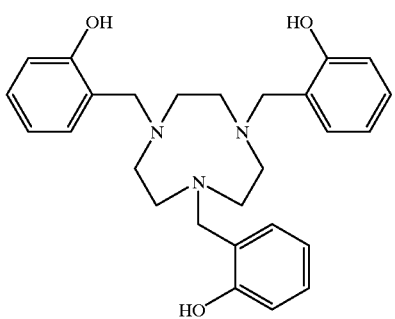

1.3.11.11

1.3.12 Synthesis of Polyaza Ligands with More Than One Species of Pendant Arm.

1.3.12.1 N-(p-Toluenesulfonyl)-N',N''-bis(diethylphosphorylmethyl)-1,4,7-triazacyclononane.

From N-(p-toluenesulfonyl)-1,4,7-triazacyclononane dihydrobromide (1.3.13.31), formaldehyde and diethyl phosphite.

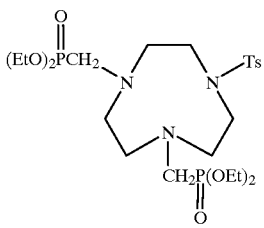

1.3.12.1

1.312.2 N,N'-Bis(diethylphosphorylmethyl)-1,4,7-triazacyclononane.

From 1,4,7-triazacyclononane (1.1.3) trihydrobromide, one equivalent formaldehyde and one equivalent of diethyl phosphite. Purification of product by chromatography.

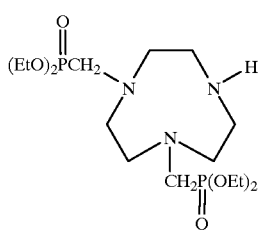

1.3.12.2

1.3.12.3 N,N'-Bis(dihydroxyphosphorylmethyl)-1,4,7-triazacyclononane.
From 1.3.12.2 and HCl.

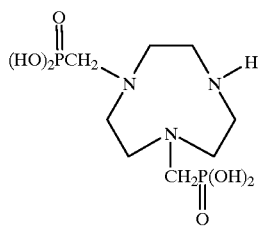

1.3.12.3

1.3.12.4 N-(Carboxymethyl)-N,N'-bis(dihydroxyphosphorylmethyl)-1,4,7-triazacyclononane.

From 1.3.12.3, chloroacetic and NaOH.

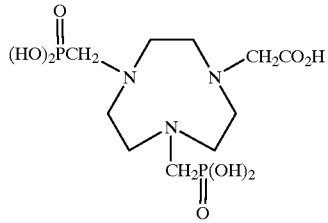

1.3.12.4

1.3.12.5 4-(2-Hydroxy-benzyl)-7-diethylphosphorylethyl-1,4,7,10-tetraazabicyclo[5.5.2]tetradecane.

From 4-(2-hydroxybenzyl)-1,4,7,10-tetraazabicyclo[5.5.2]tetradecane (1.3.11.2), diethyl phosphite and formaldehyde solution.

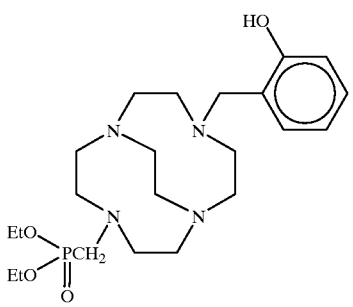

1.3.12.5

1.3.12.6 4-(2-hydroxy-benzyl)-7-phosphorylethyl-1,4,7,10-tetraazabicyclo [5.5.2]tetradecane.

From 1.3.12.5 and HCl.

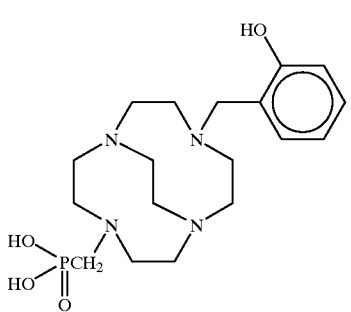

1.3.12.6

1.3.13 Miscellaneous Substituted Polyaza Compounds.

1.3.13.1 1,2-Bis-(4,7-benzyloxycarbonyl-1,4,7-triazacyclononan-1-yl)ethane.

From 1,2-bis-(1,4,7-triazacyclononan-1-yl)ethane(1.1.28) polyhydrobromide, potassium carbonate and benzyl chloroformate.

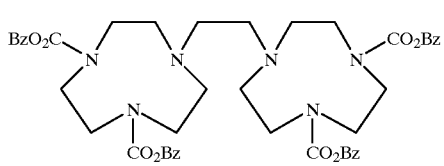

1.3.13.1

1.3.13.2 N-(p-Toluenesulfonyl)-N',N"-Bis-(benzyloxycarbonyl)-1,4,7-triazacyclononane.

From N-(p-toluenesulfonyl)-1,4,7-triazacyclononane dihydrobromide (1.3.13.31), $K_2CO_3$ and benzyl chloroformate.

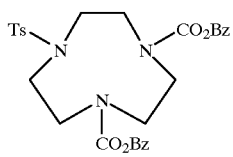

1.3.13.2

1.3.13.3 N-(p-Toluenesulfonyl)-N"-benzyloxycarbonyl-1,4,7-triazacyclononane.

From N-(p-toluenesulfonyl)-N',N"-bis(benzyloxycarbonyl)-1,4,7-triazacyclononane (1.3.13.2) and trimethylsilyl iodide.

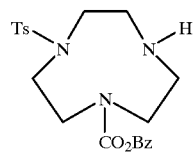

1.3.13.3

1.3.13.4 1,2-Bis[(1-p-toluenesulfonyl)-4-benzyloxycarbonyl-1,4,7-triazacyclonon-7-yl]ethane.

From 1-(p-toluenesulfonyl)-4-benzyloxycarbonyl-1,4,7-triazacyclononane (1.3.13.3), potassium carbonate and dibromoethane.

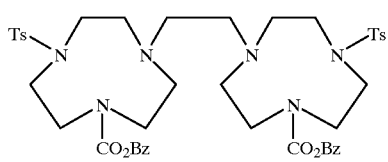

1.3.13.4

1.3.13.5 N,N',N"-Tris(phenylacetyl)-1,4,7-triazacyclononane.

From 1,4,7-triazacyclononane (1.1.3), diethyl phenylacetylphosphonate [$PhCH_2COP(O)(OEt)_2$].

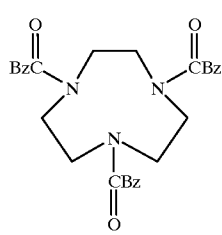

1.3.13.5

1.3.13.6 N,N',N"-Tris(2,3-Epoxypropyl-1,4,7-Triazacyclononane.

From 1,4,7-triazacyclononane (1.1.3) and epibromohydrin.

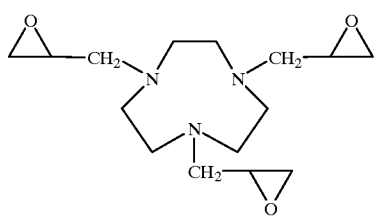

1.3.13.6

1.3.13.7 N,N',N"-Tri-allyl-1,4,7-triazacyclononane.

From 1,4,7-triazacyclononane (1.1.3), sodium hydride and allyl bromide.

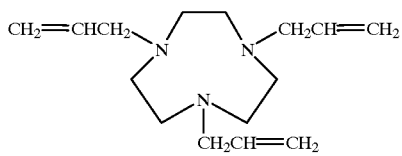

1.3.13.7

1.3.13.8 N,N',N"-Tris(benzyloxycarbonyl)-1,4,7-triazacyclononane.

From 1,4,7-triazacyclononane (1.1.3), benzyl chloroformate and sodium carbonate.

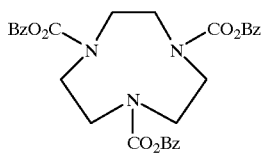

1.3.13.8

1.3.13.9 N,N'-Bis(benzyloxycarbonyl)-1,4,7-triazacyclononane.

From N,N',N"-tris(benzyloxycarbonyl)-1,4,7-triazacyclononane (1.3.13.8) and iodotrimethylsilane.

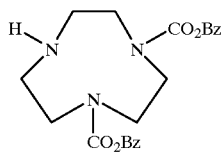

1.3.13.9

1.3.13.10 N,N'-Bis(benzyloxycarbonyl)-N"-(2-bromoethyl)-1,4,7-triazacyclononane.

From N,N'-bis(benzyloxycarbonyl)-1,4,7-triazacyclononane (1.3.13.9), dibromoethane and potassium carbonate.

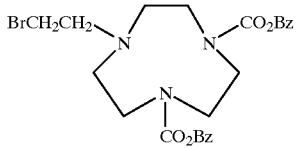

1.3.13.10

1.3.13.11 N-p-Toluenesulfonyl-N',N"-ditrifluoroacetyl-1,4,7-triazacyclononane.

From N-p-toluenesulfonyl-1,4,7-triazacyclononane (1.3.13.31), potassium carbonate and trifluoroacetic anhydride.

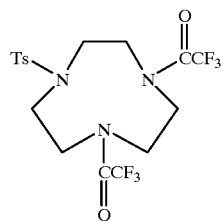

1.3.13.11

1.3.13.12 N-p-Toluenesulfonyl-N'-benzyl-1,4,7-triazacyclononane.

From N-(p-toluenesulfonyl-1,4,7-triazacyclononane (1.3.13.31), sodium hydride and benzyl bromide.

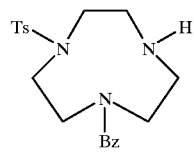

1.3.13.12

1.3.13.13 N-p-Toluenesuffonyl-N',N"-dibenzyl-1,4,7-triazacyclononane.

From N-(p-toluenesuffonyi-1,4,7-triazacyclononane (1.3.13.31), sodium hydride and benzyl bromide.

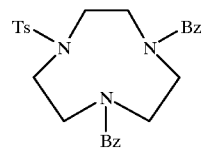

1.3.13.13

1.3.13.14 1,2-Bis(N-p-toluenesulfonyl-N'-benzyl)-1,4,7-triazacyclononan-1-yl) ethane.

From N-p-toluenesulfonyl-N'-benzyl-1,4,7-triazacyclononane (1.3.13.12), dibromoethane and potassium carbonate.

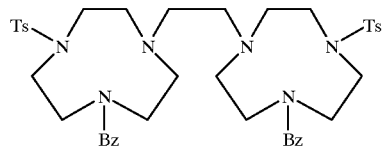

1.3.13.14

1.3.13.15 1,2-Bis(N,N'-ditrityl-1,4,7-triazacyclononan-1-yl) ethane.

From 1,2-Bis(1,4,7-triazacyclononane)ethane (1.1.28), potassium carbonate and trityl chloride.

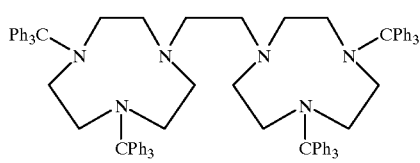

1.3.13.15

1.3.13.16 Spiro [4,8]-4,7-di-p-toluenesulfonyl-4,7-diaza-1-azotridecane halide.

From 1,4,7-triazacyclononane-N,N'-di-p-toluenesulfonyl hydrobromide (1.3.13.32), diiodobutane and potassium carbonate.

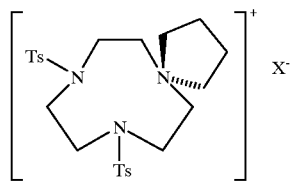

1.3.13.16

1.3.13.17 Tetrakis(p-toluenesulfonyl)-1,4,7,10-tetraazacyclotetradecane.

From N,N',N"-tris(p-toluenesulfonyl)diethylenetriamine (1.3.13.18), potassium carbonate and bis(2-p-toluenesulfonyloxyethyl)-N-(p-toluenesulfonyl) amine (1.3.13.19).

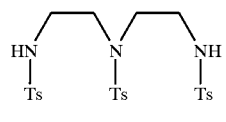

1.3.13.18

1.3.13.19

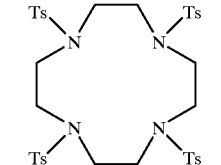

1.3.13.17

1.3.13.20 1,7-Bis(p-toluenesulfonyl)-4-benzyl-1,4,7-triazaheptane.

From benzylamine, (2-p-toluenesulfonyoxyl)-N-(p-toluenesulfonyl)-ethylamine (1.3.13.21) and potassium carbonate.

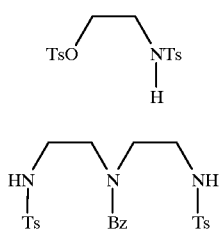

1.3.13.21

1.3.13.20

1.3.13.22 N-Trityldiethanolamine.

From diethanolamine and trityl chloride.

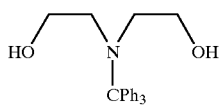

1.3.13.22

1.3.13.23 N-Trityl-bis(2-p-toluenesulfonyloxyethyl)amine.

From N-trityldiethanolamine and p-toluenesulfonyl chloride.

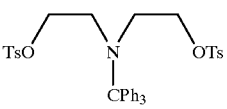

1.3.13.23

1.3.13.24 1,7-di-(p-toluenesulfonyl)-4-benzyl-10-trityl-1,4,7,10-tetraazacyclotetradecane.

From 1,7-di-p-toluenesulfonyl-4-berizyl-1,4,7-triazaheptane (1.3.13.20), sodium hydride and N-trityl-di-p-toluenesulfonyldiethanolamine (1.3.13.23).

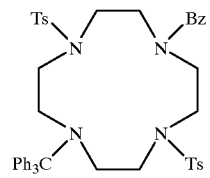

1.3.13.24

1.3.13.25 1,7-Di-(p-toluenesulfonyl)-1,4,7,10-tetraazacyclotetradecane.

From 1,7-di-(p-toluenesulfonyl)-4-benzyl-10-trityl-1,4,7,10-tetraazacyclotetradecane (1.3.13.24) reduced by $H_2$ and Pd/C.

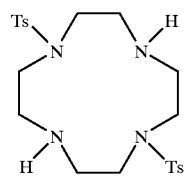

1.3.13.25

1.3.13.26 1,7-Di-(p-toluenesulfonyl)-4-benzyl-1,4,7,10-tetraazacyclotetradecane.

From reduction of 1.3.13.24.

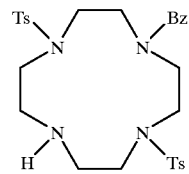

1.3.13.26

1.3.13.27 1,2-Bis-(4,10-di-p-toluenesulfonyl-7-benzyl-1,4,7,10-tetraazacyclotetradecan-1-yl)ethane.

From 1.3.13.26 and dibromoethane.

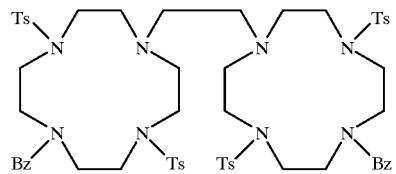

1.3.13.27

1.3.13.28 1,5,9,13-Tetraazatetracyclo[6,6,2,0$^{1,15}$, 0$^{8,16}$]hexadecane From 1.1.6 and glyoxaldehyde.

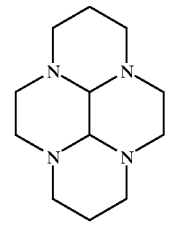

1.3.13.28

1.3.13.29 4,7-Diallyl-1,4,7-triazabicyclo[7,4,0]tridecane.

From 1,4,7-triazabicyclo[7,4,0]tridecane trihydrobromide (1.1.14), sodium hydride and allyl bromide.

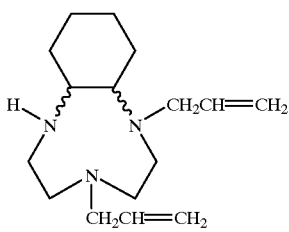

1.3.13.29

1.3.13.30 N-p-Toluenesulfonyl-1,4,7-triazacyclononane dihydrobromide.

From N,N',N"-Tris(p-toluenesulfonyl)-1,4,7-triazacyclononane (1.3.13.31) prepared from 1.3.13.18, dibromoethane and base) and HBr/acetic acid.

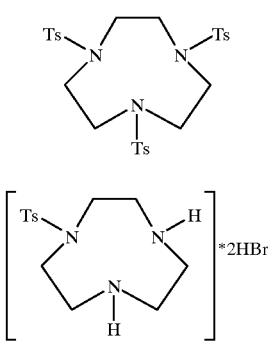  1.3.13.31

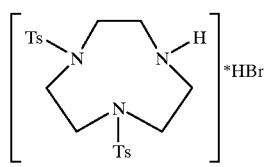  1.3.13.30

1.3.13.32 N,N'-Di-p-Toluenesulfonyl-1,4,7-triazacyclononane hydrobromide.

a) From N,N',N''-tris(p-toluenesulfonyl)-1,4,7-triazacyclononane (1.3.13.31 and HBr/acetic acid as the hydrobromide salt.

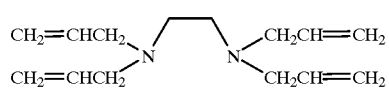  1.3.13.32

1.3.13.33 N,N,N',N'-Tetraallylethylenediamine.

From ethylenediamine, sodium carbonate and allyl bromide.

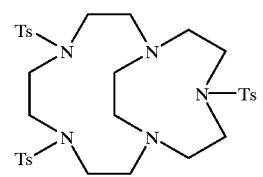  1.3.13.33

1.3.13.34 4,7,13-Tris(p-toluenesulfonyl)-1,4,7,10–13-pentaazabicyclo[8.5.2]heptadecane.

From 1,4,7,10,13-pentaazabicyclo[8.5.2]heptadecane (1.1.26), potassium carbonate and p-toluenesulfonyl chloride.

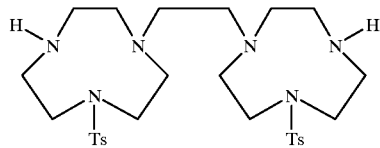  1.3.13.34

1.3.13.35 1,2-Bis(4-p-toluenesulfonyl-1,4,7-triazacyclonon-1-yl)ethane.

From 1,2-bis(4,7-di-p-toluenesulfonyl-1,4,7-triazacyclonon-1-yl)ethane (1.1.30) and sulphuric acid.

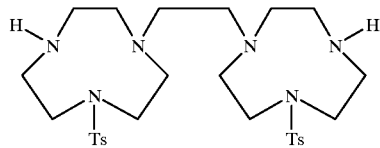  1.3.13.35

1.3.13.36 N,N'-(Di-p-toluenesulfonyl)-N''-benzyl-1,4,7-Triazacyclononane.

a) From N,N''-(p-toluenesulfonyl)-4-benzyl diethylenetriamine (1.3.13.20), sodium hydride and ethylene glycol di-p-toluenesulfonate (1.1.1 2).

b) From N,N'-bis(p-toluenesulfonyl)-1,4,7-triazacyclononane (1.3.13.32), sodium hydride and benzyl bromide.

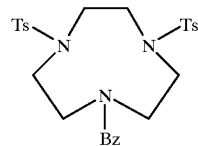  1.3.13.36

1.3.13.37 N-(p-Toluenesulfonyl)-N'-trityl-1,4,7-triazacyclononane.

From N-(p-toluenesulfonyl-1,4,7-triazacyclononane dihydrobromide (1.3.13.30), sodium hydride and trityl chloride.

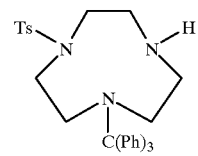  1.3.13.37

1.3.13.38 Hexakis(allyl) triethylenetetramine.

From triethylenetetramine (1.1.2), sodium carbonate and ally bromide.

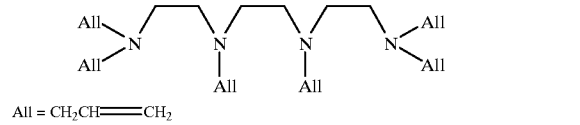  1.3.13.38

All = $CH_2CH{=}CH_2$

1.3.13.39 4,7-diallyl-1,4,7,10-tetraazabicyclo[5.5.2]tetradecane.

From 1,4,7,10-tetraazabicyclo[5.5.2]tetradecane (1.1.4), allyl bromide and base.

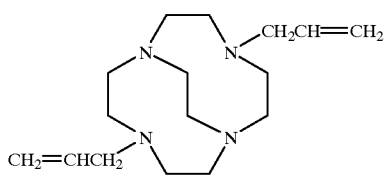

1.3.13.39

This example illustrates the ability of the chelating agents described above to inhibit cell replication in vitro.

2.1: INHIBITION OF BACTERIAL REPLICATION

This example demonstrates the ability of a representative example of the claimed ligands to inhibit replication of various bacteria in vitro.

N,N',N"-tris(dihydroxyphosphorylmethyl)-1,4,7-triazacyclononane was prepared as described in Example 1C in U.S. Pat. No. 5,236,695. Studies were performed to determine its ability to inhibit bacterial growth. For *Streptococcus hemolyticus, Listeria monocytogenes, Enterobacter cloacae* and *Klebsiella pneumoniae* the minimum inhibitory concentration was determined to be 0.15 mM/L. For *Enterococcus fecals, Pseudomonas aeruginosa* and *Acinobacter anitratus* the minimum inhibitory concentration was determined to be 0.3 mM/L.

2.2: INHIBITION OF MYCOTIC CELL REPLICATION IN VITRO

This example demonstrates the ability of a representative example of the claimed ligands to inhibit mycotic (fungal) cell replication in vitro.

N,N',N"-tris(dihydroxyphosphorylmethyl)-1,4,7-triazacyclononane was prepared as described in Example 1C in U.S. Pat. No. 5,236,695. Studies were performed to determine its ability to inhibit growth of mycotic (fungal) organisms.

For *Microsporum canis* the minimum inhibitory concentration was 0.233 mM/L or less. For *Candida albicans* and *Trichophyton rubrum* the minimal inhibitory concentration was 2.33 mM/L. For *Trichophyton mentagrophytes, Trichophyton tonsuras* and *Trichophyton violaceum* the minimal inhibitory concentration was 23.3 mM/L.

2.3: INHIBITION OF MAMMALIAN CELL REPLICATION IN VITRO

This example demonstrates the ability of representative examples of the claimed ligands to inhibit mammalian cell replication in vitro.

N,N',N"-tris(dihydroxyphosphorylmethyl)-1,4,7-triazacyclononane was prepared as described in Example 1C in U.S. Pat. No. 5,236,695.

Concentrations of this ligand of 0.009 mM/L inhibited the growth of both BGM cells (a continuous cell line of monkey origin) and HFF cells (human foreskin fibroblasts).

N,N',N"-Tris(carboxymethyl)-1,4,7-Triazacyclononane (Example 1.3.6.1) at a concentration of 0.009 mM/L inhibited BGM cell growth and a concentration of 0.019 mM/L inhibited HFF cell growth.

N,N',N"-Tris(ethoxycarbonylmethyl)-1,4,7-Triazacyclononane (Example 1.3.6.13) at a concentration of 0.04 mM/L inhibited BGM cell growth and at a concentration of 0.16 mM/L inhibited HFF cell growth. Diethylene triamine penta acetic acid at a concentration of 0.075 mM/L inhibited BGM cell growth and at 0.3 mM/L inhibited HFF cell growth.

Example 3

This example demonstrates the relative lack of toxicity of a representative example of the claimed ligands toward nonproliferating mammalian cells in vitro.

N,N',N"-tris(dihydroxyphosphorylmethyl)-1,4,7- triazacyclononane was prepared as described in Example 1C in U.S. Pat. No. 5,236,695.

A concentration of 0.3 mM of this agent was added to mature, nonreplicating cultures of HFF (human foreskin fibroblasts) kept in maintenance media and no effect on the resting cells was observed over a five-day period of observation.

Example 4

This example illustrates the low in vivo toxicity of a representative ligand administer intravenously to mice.

Over 50% of mice receiving 4.0 mM/kg intravenously of the sodium salt of N,N',N"-tris-(dihydroxyphosphorylmethyl)-1,4,7-triazacyclononane (Example 1C in U.S. Pat. No. 5,236,695) as a single intravenous dose survived for over 14 days following such administration demonstrating that the acute LD50 of this agent is in excess of 4 mM/kg. This in vivo LD50 toxicity dose results in an instantaneous in vivo concentration which is orders of magnitude greater than the dose of this agent which inhibits mammalian cell replication in vitro (0.009 mM/L).

Example 5

This example demonstrates the relatively low subacute toxicity of a representative ligand administered intravenously in repeated doses to rats.

Ten male Sprague Dawley rats 29 days old and weighing between 73.4 and 87.8 grams at the beginning of the experiment were randomized, employing the block stratification method, into two groups consisting of five rats each. On each of days 1, 2, 3, 6, 7, 8, 9, 10, 13 and 14 of the experiment one set of rats received an intravenous dose of N,N',N"-tri(dihydroxy-phosphoryl methyl)-1,4,7-triazacyclononane (Example 1C in U.S. Pat. No. 5,236,695) equal to 0.05 millimoles per kg of initial body weight (experimental group) while the other group received an equivalent volume of normal saline solution. The weights of the animals were recorded three times per week and the animals were sacrificed on the 28th day, major organs removed and weighed and tissues removed for microscopic examination. There was no statistically significant difference in weight or rate of weight gain between the experimental and control group of rats, either during the period of injections or in the two-week post-injection period. There were no differences observed between the weights of major organs of the experimental vs. the control group. There were no differences between the tissues of the experimental vs. the control group upon microscopic examination of the tissues obtained at the time of necropsy.

Example 6

Inhibition of Underarm Odor

Human subjects applied a 30% aqueous solution of the neutral sodium salt of N,N',N"-tri(dihydroxyphosphoryl methyl)-1,4,7-triaza-cyclononane in one axilla and a control aqueous solution in the other. Subjective evaluation of underarm odor demonstrated less underarm odor in the treated axilla than in the control. A single application of the agent resulted in decreased underarm odor for up to one week following application.

Example 7
Inhibition of the Cariogenic Bacteria *Streptococcus Sobrinus*

Employing RPMI medium the minimum inhibitory concentration (MIC) for N,N',N"-tri(dihydroxyphosphoryl methyl)-1,4,7-triazacyclononane against *Streptococcus Sobrinus* was found to be less than 0.02 mM.

Example 8
Chemical Antioxidant Properties

Antioxidant properties of N,N',N"-tri (dihydroxyphosphoryl methyl)-1,4,7-triazacyclononane were evaluated employing the coupled oxidation of carotene and linoleic acid, using the method described in "Phenolic Antioxidants of Dried Soybeans," Hammerschmidt, P. A., Praat, D. E., 1978, *Journal of Food Sciences*, vol. 43, pp. 556–559. The agent proved to have antioxidant activity similar to the commonly used food antioxidant butylated hdryoxyanisole (BHA).

Example 9
Inhibition of Iron-Catalyzed Free Radical Generation Through Fenton Reactions Employing published methods, as described in "Quantitative Effects of Iron Chelators on Hydroxyl Radical Production by the Superoxide-Driven Fenton Reaction," J. B. Smith, J. C. Cusumano, C. F. Babbs, *Free Rad. Res. Comms.* 1990, Vol. 8, No. 2, 101–106, the ability of Fe(III) complexed to N,N',N"-tri(dihydroxyphosphoryl methyl)-1,4,7-triazacyclononane to support Fenton reactions was evaluated. Fe(III) complexed by EDTA was used as a positive control and supported the Fenton reaction yielding hydroxyl radicals while Fe(III) complexed to 3MP failed to show evidence of hydroxyl ion formation above background.

Example 10
Inhibition of Metalloenzymes

Matrix metalloproteinase-2 (MMP-2) secreted by cells into growth media was separated by gel electrophoresis into its distinct band. Incubation in developing medium without and with varying concentrations of salts of N,N',N"-tri (dihydroxyphosphoryl methyl)-1,4,7-triazacyclononane demonstrated that less than 10 microM concentrations of the agent inhibited enzymatic action. Employing pure MMP-2 enzyme, it was established that the sodium salt of N,N',N"-tri(dihydroxyphosphoryl methyl)-1,4,7-triaza-cyclononane had an $IC_{50}$ of less than 10 microM. Concentrations of less than 10 microM of sodium salt of N,N',N"-tri (dihydroxyphosphoryl methyl)-1,4,7-triazacyclononane inhibited monocyte penetration of Matrigel membranes.

Example 11
Inhibition of Hypoxia Reperfusion Injury

Using the ischemic/reperfused isolated working rat heart model of Ferdinandy et al., *Cardiovasc. Res.*, 1995; 30:781–787, concentrations at least as low as 0.1 mM of various salts of N, N', N"-tris(dihydroxyphosphoryl-methyl)-1,4,7-triazacyclononane in the perfusing medium were found to be effective in improving myocardial functional parameters and decreasing the incidence of ventricular fibrillation. Concentrations of this agent as high as 7.2 mM had no adverse effects on the heart either before or after hypoxia/reperfusion injury.

Example 12
Inhibition of In Vitro Proliferation of Human Cancer Cells

The ability of N-methyl-N',N"-bis (dihydroxyphorylmethyl)-1,4,7-triazacyclononane to inhibit proliferation of 57 human cancer cell lines in vitro was evaluated employing published methods as published in *J. Natl. Cancer Inst.*, 83:757–766, 1991. The concentration of agent that caused 50% inhibition of cell replication relative to controls [$GI_{50}$] were determined. In one set of experiments the mean midpoint of $GI_{50}$ for all cell lines tested was $(10)^{-4.72}$ with a delta value of $(10)^{2.95}$ and a range of $(10)^{3.67}$. As a group, leukemia and colon cancer cells were more sensitive to the agent than were other cancer cells.

Example 13
Inhibition of In AIDS Virus Replication

The antiviral efficacy of N,N',N"-tris(5-t-butyl-2-hydroxy-benzyl)-1,4,7-triazacyclononane against the AIDS virus was evaluated employing published methodology (see, "New Soluble-Formazin Assay for HIV-1 Cytopathic Effects: Application to High Flux Screening of Synthetic and Natural Products for AIDS-Antiviral Activity," *J. Natl. Cancer Inst.* 81:577–586, 1989). In cytotoxicity studies, the T4 lymphocyte was found to show an $IC_{50}$ value of 0.11 mM while inhibition studies of the AIDS Virion showed an $EC_{50}$ value of 0.003 mM.

Those skilled in the art will recognize that:

Examples 6–9 demonstrate the utility of the subject agents in cosmetics and personal care products. Example 6 demonstrates utility in inhibiting development of body odors thus demonstrating the usefulness of the agents in deodorant products. Example 7 demonstrates the ability of the subject agents to inhibit growth of *Strep. Sobrinus*, an example of a microorganism implicated in tooth decay, thereby demonstrating the utility of the subject agents in oral care products. Example 8 demonstrates the ability of the subject agents to inhibit chemical oxidation and Example 9 demonstrates that when Fe(III) is complexed by these agents it no longer can catalyze hydroxyl free radical formation. Examples 8 and 9 together demonstrate the utility of these agents as inhibitors of oxidative damage in skin and hair personal care products. Example 10 demonstrates that the subject agents can inhibit metalloenzyme activity for enzymes containing first transition series elements. Example 11 demonstrates that the subject agents can inhibit hypoxia/reperfusion tissue injury. This finding is also supported by Examples 9 and 10 since hypoxia/reperfusion injury is believed, at least in part, to be caused by tissue damage caused by free radicals and by action of matrix metalloproteinases.

What is claimed is:

1. A method for inhibiting body odors in a subject comprising administering to said subjet cosmetic/personal are products into which are incorporated a complexing agent having the formula

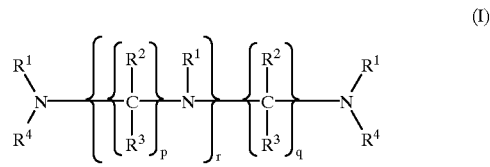

(I)

wherein, p and q are independently integers of from 2 to 3;

r is an integer of from 1 to 4;

$R^2$, $R^3$, and $R^4$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^1$ is a member selected from the group consisting of $R^2$, $R^3$, $R^4$, and radicals of the formula:

$$\text{—}\underset{R^{42}}{\overset{R^{41}}{\underset{|}{C}}}\text{—}\left[\underset{R^{44}}{\overset{R^{43}}{\underset{|}{C}}}\right]_n\text{—}X \quad (V)$$

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, alikenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^1$, $R^2$, $R^3$ and $R^4$ are combined to form a ring structure;

and dimers of Formula I, said dimers being formed by the covalent attachment of two complexing agents of Formula I through a linking group having from 1 to 6 carbon atoms; and physiological salts thereof;

with the proviso that the molecular weight of said complexing agent does not exceed 2000.

2. A method of inhibiting tooth decay, gum disease and periodontal disease in a subject, comprising administering to said subject an oral care product incorporating a complexing agent having the formula:

(I)

wherein, p and q are independently either 2 or 3;

r is an integer of from 1 to 4;

$R^2$, $R^3$, and $R^4$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^1$ is a member selected from the group consisting of $R^2$, $R^3$, $R^4$, and radicals of the formula:

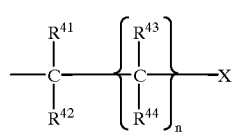

(V)

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

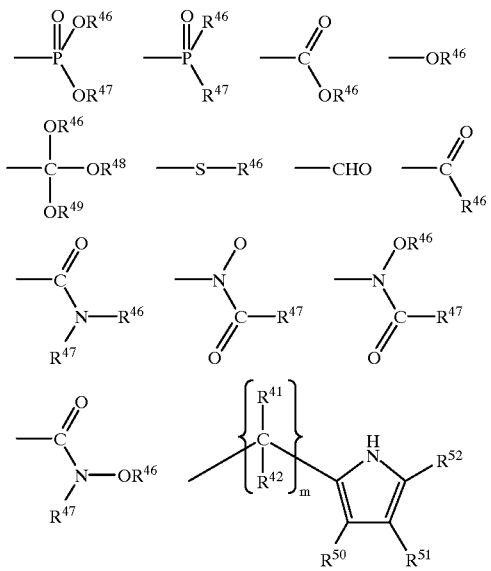

-continued

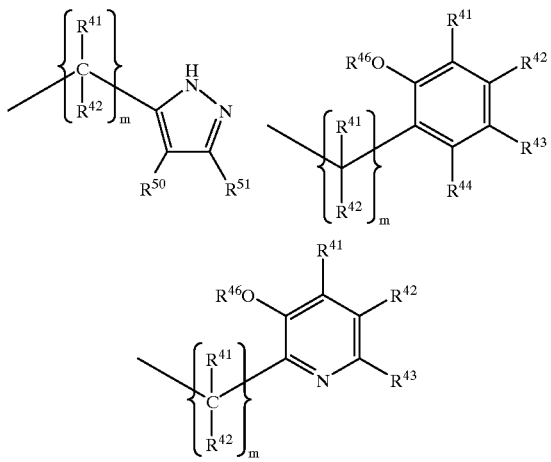

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, alikenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^1$, $R^2$, $R^3$ and $R^4$ are combined to form a ring structure;

and dimers of Formula I, said dimers being formed by the covalent attachment of two complexing agents of Formula I through a linking group having from 1 to 6 carbon atoms; and physiological salts thereof;

with the proviso that the molecular weight of said complexing agent does not exceed 2000.

3. A method of inhibiting metalloenzymes containing first transition series metal cations in a subject, comprising administering or applying to said subject a complexing agent having the formula:

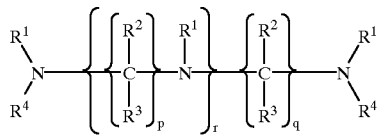

(I)

wherein, p and q are independently either 2 or 3;

r is an integer of from 1 to 4;

$R^2$, $R^3$, and $R^4$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^1$ is a member selected from the group consisting of $R^2$, $R^3$, $R^4$, and radicals of the formula:

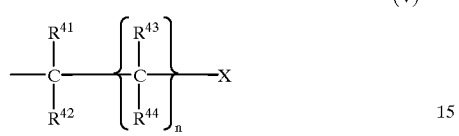

(V)

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

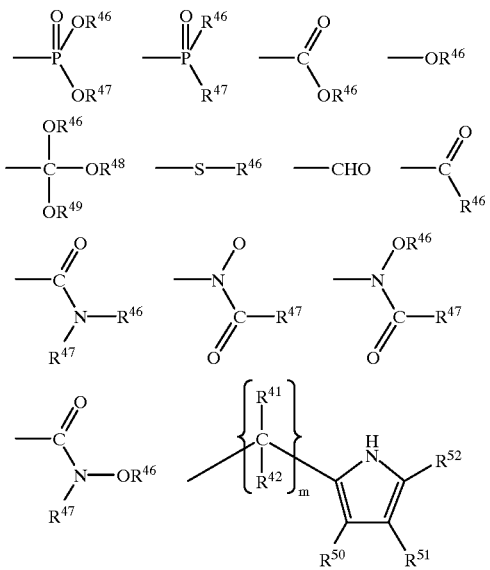

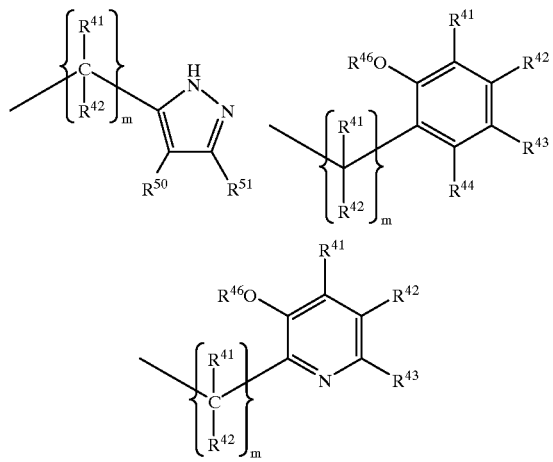

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^1$, $R^2$, $R^3$ and $R^4$ are combined to form a ring structure;

and dimers of Formula I, said dimers being formed by the covalent attachment of two complexing agents of Formula I through a linking group having from 1 to 6 carbon atoms; and physiological salts thereof;

with the proviso that the molecular weight of said complexing agent does not exceed 2000.

4. A method of inhibiting reperfusion injury in a subject, comprising administering to said subject a complexing agent having the formula:

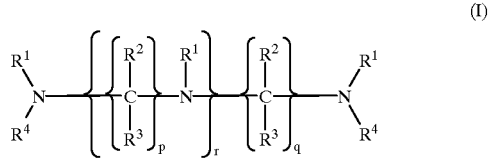

(I)

wherein, p and q are independently integers of from 2 to 3;

r is an integer of from 1 to 4;

$R^2$, $R^3$, and $R^4$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^1$ is a member selected from the group consisting of $R^2$, $R^3$, $R^4$, and radicals of the formula:

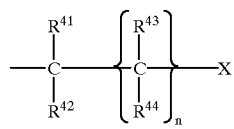

(V)

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

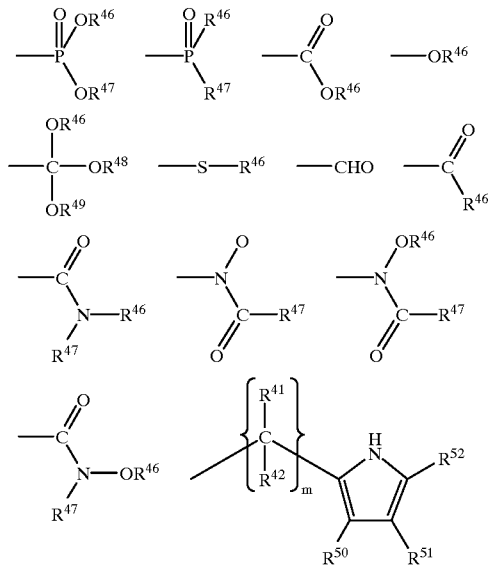

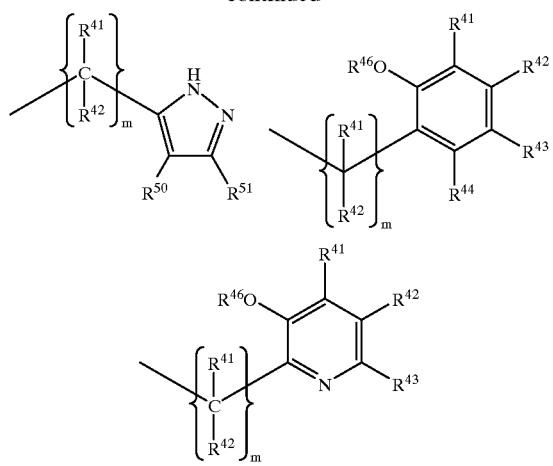

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^1$, $R^2$, $R^3$ and $R^4$ are combined to form a ring structure;

and dimers of Formula I, said dimers being formed by the covalent attachment of two complexing agents of Formula I through a linking group having from 1 to 6 carbon atoms; and physiological salts thereof;

with the proviso that the molecular weight of said complexing agent does not exceed 2000.

5. A method for inhibiting body odors in a subject comprising administering to said subject a cosmetic/personal care product into which is incorporated a complexing agent having the formula

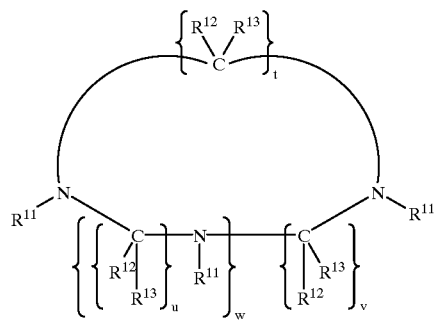

(II)

wherein, t, u and v are each independently 2 or 3;

w is an integer of from 1 to 4;

$R^{11}$ and $R^{13}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{11}$ is a member selected from the group consisting of $R^{11}$, $R^{12}$ and radicals of the formula:

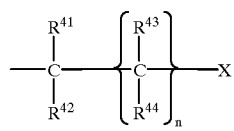

(V)

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

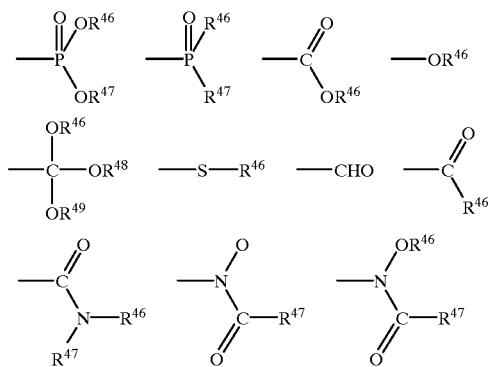

-continued

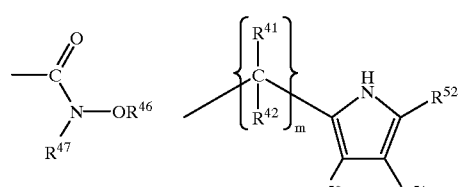

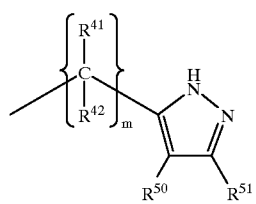 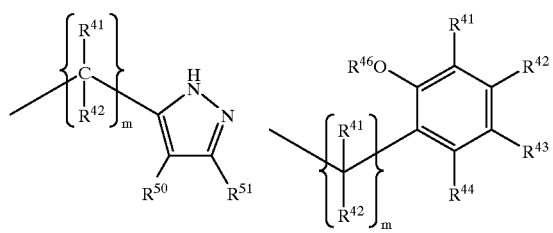

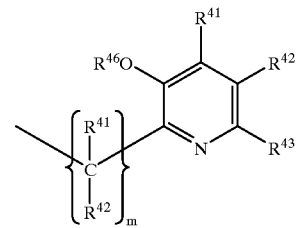

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^{11}$, $R^{12}$, and $R^{13}$ are combined to form a ring structure;

and dimers of Formula II, said dimers being formed by the covalent attachment of two complexing agents of Formula II through a linking group having from 1 to 6 carbon atoms; and physiological salts thereof;

with the proviso that the molecular weight of said complexing agent does not exceed 2000.

6. A method for inhibiting tooth decay, gum disease and periodontal disease in a subject comprising administering to said subject an oral care product into which is incorporated a complexing agent having the formula

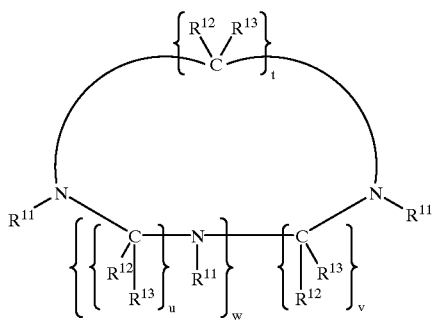

(II)

wherein, t, u and v are each independently 2 or 3;

w is an integer of from 1 to 4;

$R^{11}$ and $R^{13}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{11}$ is a member selected from the group consisting of $R^{11}$, $R^{12}$ and radicals of the formula:

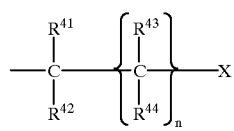

(V)

wherein, $R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;

$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;

n is zero or 1; and

X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

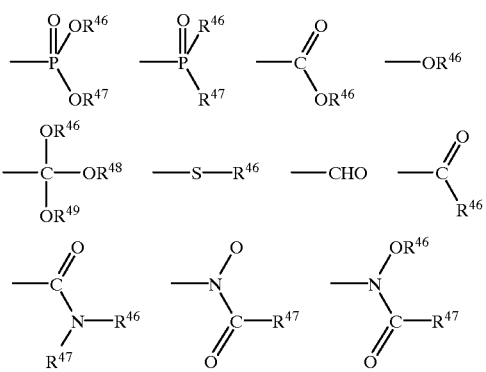

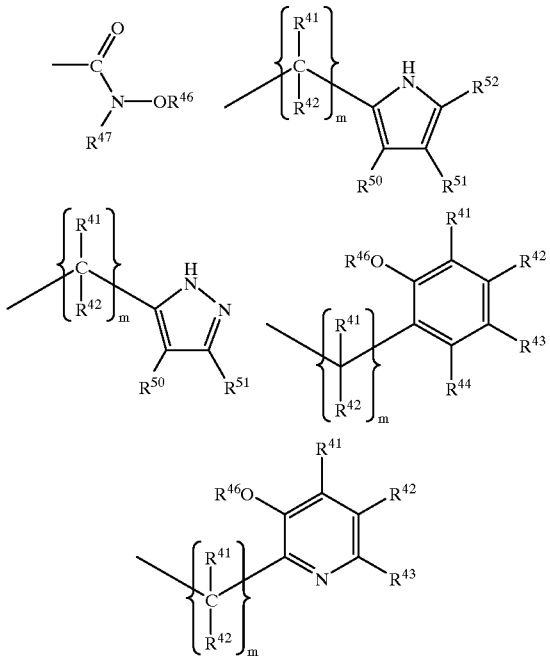

wherein, $R^{41}$, $R^{42}$, $R^{43}$ and $R^{44}$ are each independently as defined above;

$R^{46}$ and $R^{47}$ are each independently selected from the group consisting of H, alkyl and aryl, or taken together form a ring structure;

$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;

$R^{50}$, $R^{51}$ and $R^{52}$ are each independently selected from the group consisting of H, alkyl, alkenyl, aryl, arylalkyl, alkoxy, alkylthio, alkenyloxy, alikenylthio, aryloxy, aminoalkyl, aminoalkenyl, aminoaryl, aminoarylakyl, hydroxyalkyl, hydroxyalkenyl, hydroxyaryl, and hydroxyarylalkyl; and m is an integer of from 1 to 3 and wherein, optionally, any two of $R^{11}$, $R^{12}$, and $R^{13}$ are combined to form a ring structure;

and dimers of Formula II, said dimers being formed by the covalent attachment of two complexing agents of Formula II through a linking group having from 1 to 6 carbon atoms; and physiological salts thereof;

with the proviso that the molecular weight of said complexing agent does not exceed 2000.

7. A method for inhibiting metalloenzymes containing first transition series elements in a subject comprising administering to said subject a complexing agent having the formula (II)

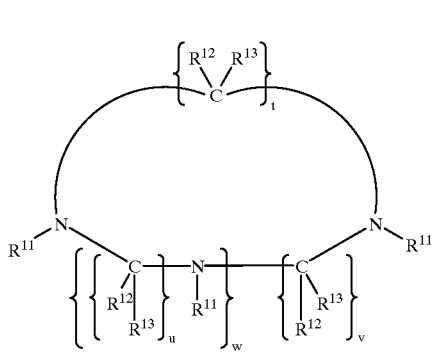

wherein,
t, u and v are each independently 2 or 3;
w is an integer of from 1 to 4;
$R^{11}$ and $R^{13}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;
$R^{11}$ is a member selected from the group consisting of $R^{11}$, $R^{12}$ and radicals of the formula:

(V)

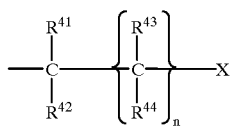

wherein,
$R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;
$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;
n is zero or 1; and
X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

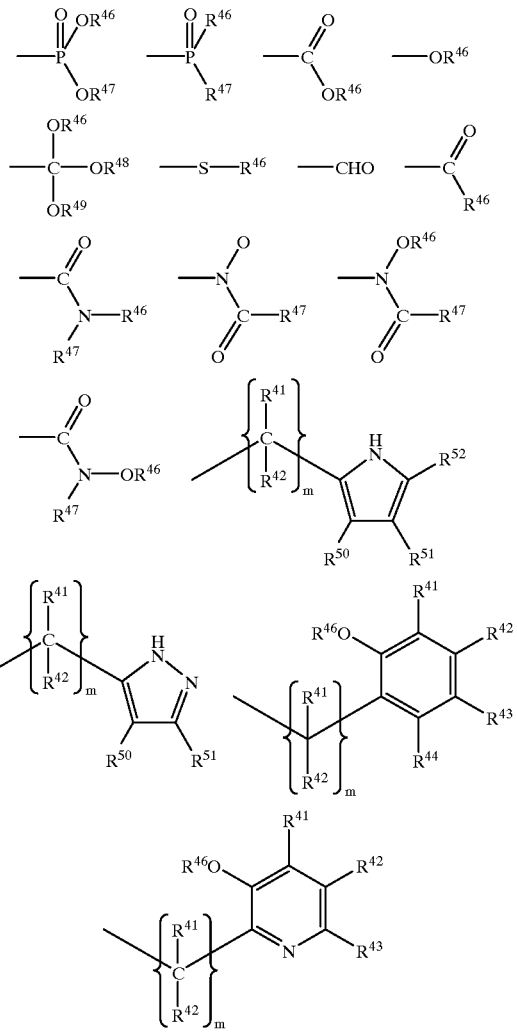

wherein,
$R^{41}$, $R^{42}$, $R^{43}$ and $R^{44}$ are each independently as defined above;
$R^{46}$ and $R^{47}$ are each independently selected from the group consisting of H, alkyl and aryl, or taken together form a ring structure;
$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;
$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and
m is an integer of from 1 to 3
and wherein, optionally, any two of $R^{11}$, $R^{12}$, and $R^{13}$ are combined to form a ring structure;
and dimers of Formula II, said dimers being formed by the covalent attachment of two complexing agents of Formula II through a linking group having from 1 to 6 carbon atoms; and physiological salts thereof;

with the proviso that the molecular weight of said complexing agent does not exceed 2000.

8. A method for inhibiting reperfusion injury in a subject comprising administering to said subject a complexing agent having the formula

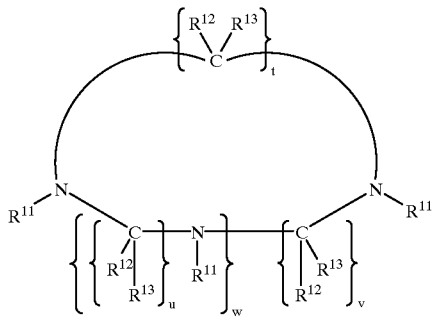

(II)

wherein,
t, u and v are each independently 2 or 3;
w is an integer of from 1 to 4;
$R^{11}$ and $R^{13}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;
$R^{11}$ is a member selected from the group consisting of $R^{11}$, $R^{12}$ and radicals of the formula:

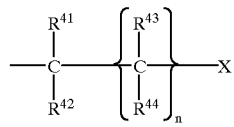

(V)

wherein,
$R^{41}$, $R^{42}$, and $R^{43}$ are each independently selected from the group consisting of H, alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, and halogen-substituted versions thereof;
$R^{44}$ is a member selected from the group consisting of H, hydroxy, amino, alkyl interrupted by oxa, alkoxy, aryl, aryloxyalkyl, alkoxyaryl, alkoxyaryl, and halogen-substituted versions thereof;
n is zero or 1; and
X is a member selected from the group consisting of alkyl, alkenyl, aryl, arylalkyl, alkoxy, alkylthio, alkenoxy, alkenylthio, aryloxy, arylthio, alkyl interrupted by oxa, alkenyl interrupted by oxa, alkyl interrupted by thia, alkenyl interrupted by thia, aryloxyalkyl, alkoxyaryl, aminoalkyl, aminoalkenyl, aminoaryl, aminoarylalkyl, hydroxyalkyl, hydroxyalkenyl, hydroxyaryl, hydroxyarylalkyl, halogen-substituted versions thereof, and radicals selected form the group consisting of:

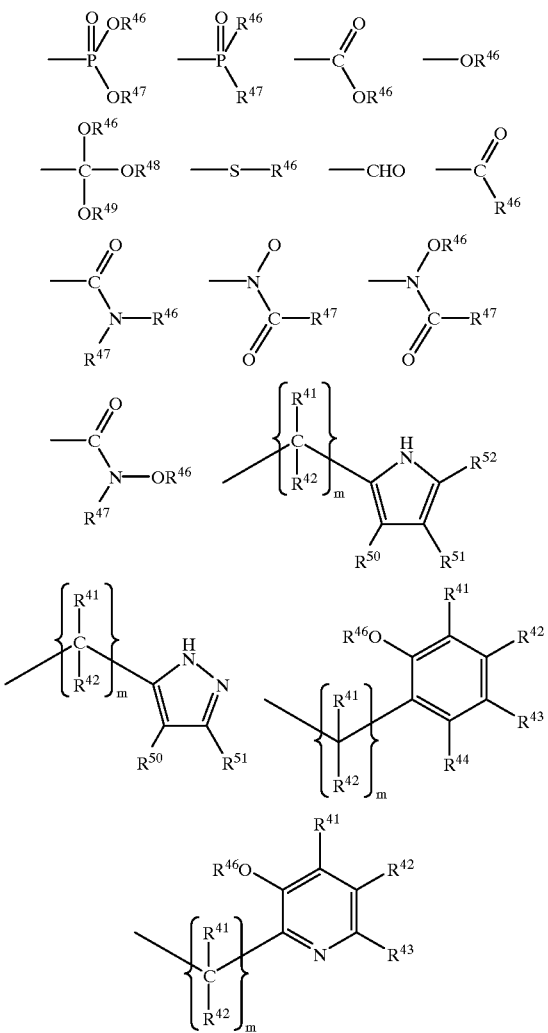

wherein,
$R^{41}$, $R^{42}$, $R^{43}$ and $R^{44}$ are each independently as defined above;
$R^{46}$ and $R^{47}$ are each independently selected from the group consisting of H, alkyl and aryl, or taken together form a ring structure;
$R^{48}$ and $R^{49}$ are each independently selected from the group consisting of H, alkyl, aryl, alkoxy, alkyl interrupted by oxa, aryloxyalkyl, alkoxyaryl, and halogen-substituted versions thereof;
$R^{50}$, $R^{51}$ and $R^{52}$ are each independently selected from the group consisting of H, alkyl, alkenyl, aryl, arylalkyl, alkoxy, alkylthio, alkenyloxy, allkenylthio, aryloxy, aminoalkyl, aminoalkenyl, aminoaryl, aminoarylakyl, hydroxyalkyl, hydroxyalkenyl, hydroxyaryl, and hydroxyarylalkyl; and
m is an integer of from 1 to 3
and wherein, optionally, any two of $R^{11}$, $R^{12}$, and $R^{13}$ are combined to form a ring structure;
and dimers of formula II, said dimers being formed by the covalent attachment of two complexing agents of Formula II through a linking group having from 1 to 6 carbon atoms; and physiological salts thereof;

with the proviso that the molecular weight of said complexing agent does not exceed 2000.

9. A method in accordance with claim 5 in which said complexing agent is N,N',N"-tri(dihydroxyphosphorylmethyl)-1,4,7-triaza-cyclononane.

10. A method in accordance with claim 6 in which said complexing agent is N,N',N"-tri(dihydroxyphosphorylmethyl)-1,4,7-triaza-cyclononane.

11. A method in accordance with claim 7 in which said complexing agent is N,N',N"-tri(dihydroxyphosphorylmethyl)-1,4,7-triaza-cyclononane.

12. A method in accordance with claim 8 in which said complexing agent is N,N',N"-tri(dihydroxyphosphorylmethyl)-1,4,7-triaza-cyclononane.

\* \* \* \* \*

UNITED STATES PATENT AND TRADEMARK OFFICE
CERTIFICATE OF CORRECTION

PATENT NO. : 6,264,966 B1
DATED : July 24, 2001
INVENTOR(S) : Winchell et al.

It is certified that error appears in the above-identified patent and that said Letters Patent is hereby corrected as shown below:

Column 73,
Line 31, replace "alkoxyaryl, alkoxyaryl," with -- alkoxyaryl, --

Column 75,
Line 32, replace "alkoxyaryl, alkoxyaryl," with -- alkoxyaryl, --

Column 77,
Line 32, replace "alkoxyaryl, alkoxyaryl," with -- alkoxyaryl, --

Column 79,
Line 31, replace "alkoxyaryl, alkoxyaryl," with -- alkoxyaryl, --

Column 81,
Line 5, replace "$R^{11}$", with -- $R^{12}$ --
Line 16, replace "$R^{11}$, $R^{12}$" with -- $R^{12}$, $R^{13}$ --
Line 39, replace "alkoxyaryl, alkoxyaryl," with -- alkoxyaryl, --

Column 83,
Line 21, replace "$R^{11}$", with -- $R^{12}$ --
Line 32, replace "$R^{11}$, $R^{12}$" with -- $R^{12}$, $R^{13}$ --
Line 55, replace "alkoxyaryl, alkoxyaryl," with -- alkoxyaryl, --

Column 85,
Line 24, replace "$R^{11}$", with -- $R^{12}$ --
Line 35, replace "$R^{11}$, $R^{12}$" with -- $R^{12}$, $R^{13}$ --
Line 58, replace "alkoxyaryl, alkoxyaryl," with -- alkoxyaryl, --

UNITED STATES PATENT AND TRADEMARK OFFICE
CERTIFICATE OF CORRECTION

PATENT NO.    : 6,264,966 B1
DATED         : July 24, 2001
INVENTOR(S)   : Winchell et al.

It is certified that error appears in the above-identified patent and that said Letters Patent is hereby corrected as shown below:

<u>Column 87,</u>
Line 25, replace "$R^{11}$", with -- $R^{12}$ --
Line 36, replace "$R^{11}$, $R^{12}$" with -- $R^{12}$, $R^{13}$ --
Line 59, replace "alkoxyaryl, alkoxyaryl," with -- alkoxyaryl, --

Signed and Sealed this

Second Day of September, 2003

JAMES E. ROGAN
*Director of the United States Patent and Trademark Office*